US005719021A

United States Patent [19]

Inouye

[11] Patent Number: 5,719,021
[45] Date of Patent: *Feb. 17, 1998

[54] PROTEIN ACTIVATION

[75] Inventor: Masayori Inouye, Bridgewater, N.J.

[73] Assignee: University of Medicine and Dentistry of New Jersey, Newark, N.J.

[*] Notice: The term of this patent shall not extend beyond the expiration date of Pat. No. 5,191,063.

[21] Appl. No.: 923,260

[22] Filed: Jul. 31, 1992

Related U.S. Application Data

[63] Continuation-in-part of Ser. No. 346,552, May 2, 1989, Pat. No. 5,191,063.

[51] Int. Cl.$^6$ .............................. C12Q 11/68; C12P 21/00; C12N 9/96; C07K 14/435
[52] U.S. Cl. .................................................. 435/6
[58] Field of Search .......................... 435/6, 68.1, 69.1, 435/183, 188; 530/324, 345, 350, 402, 427

[56] References Cited

U.S. PATENT DOCUMENTS 5,191,063  3/1993  Inouye et al. ............................ 530/324

FOREIGN PATENT DOCUMENTS 396106  11/1990  European Pat. Off. .

OTHER PUBLICATIONS

Silen et al. (1989) Nature, vol. 341, pp. 462–464.
Suter et al. (1991) EMBO Journal, vol. 10, No. 9, pp. 2395–2400.
Zhu et al. (1989) Nature, vol. 339, pp. 483–484.

*Primary Examiner*—Mindy Fleisher
*Assistant Examiner*—Nancy J. Degen
*Attorney, Agent, or Firm*—Weiser & Associates, P.C.

[57] ABSTRACT

A method is disclosed for producing a biochemically active polypeptide from a biochemically inactive polypeptide. The polypeptide is normally but need not be expressed in a precursor form containing a pro-sequence. The inactive polypeptide is reacted with a tailor-made activating peptide. The activating peptide can be synthetic or made by recombinant DNA procedure. The activating peptide is a peptide which contains one or more functional domains which are necessary for folding the inactive polypeptide into a biochemically active conformation. The activating peptide may but need not contain a sequence of amino acids which is identical to the sequence of the natural occurring pro-sequence of the polypeptide. Also, a method is disclosed which permits to identify the one or more functional domains in the pro-sequence of a polypeptide which contribute(s) to the folding of the inactive polypeptide into a biochemically active conformation. The invention relates also to a tailor-made activating peptide (synthetic or by recombinant DNA) and to the biochemically active polypeptide. The protein activation method and the biochemically active proteins are of major utility in their broad applications.

23 Claims, 5 Drawing Sheets
(1 of 5 Drawing(s) in Color)

```
Bacillus subtilis 168        ------->  subtilisin E
Bacillus amyloliquefaciens   ------->  subtilisin BPN'
Bacillus amylosaccchariticus ------->  subtilisin Amylosacchariticus
Bacillus licheniformis       ------->  subtilisin Carlsberg
```

```
PRO-    -70        -60        -50        -40        -30        -20        -10
         |          |          |          |          |          |          |
        AGKSSTEKKYIVGFKQTMSAMSSAKKKDVISEKGGKVQKQFKYVNAAAATLDEKAVKELKKDPSVAYVEEDHIAHEY
              NG           TA           IKS  D  RII  DSN  KK  KE   LVN D            V
              NG           TA           ASV                                         V
        AQPAKNV D  -SSGVKT                  D    N                       D          V  L

MATURE- 10         20         30         40         50         60         70         80         90        100
         |          |          |          |          |          |          |          |          |          |
        AQSVPYGISQIKAPALHSQGYTGSNVKVAVIDSGIDSSHPDLNVRGGASFVPSETNPYQDGSSHGTHVAGTIAALNNSIGVLGVSPSASLYAVKVLDSTG
                                                KAM        V            NN                              D TT        V          GA
                                                 QA        V          AG A-YN T NG                                             NS 110        120        130        140        150        160        170        180        190        200
         |          |          |          |          |          |          |          |          |          |
        SGQYSWIINGIEWAISNNMDVINMSLGGPTGSTALKTVVDKAVSSGIVAAAAGNEGSSGSTSTVGYPAKYPSTIAVGAVNSSNQRASFSSAGSELDVMA
         N               A                 S   A   AA   A V   T      S   G   V   D                   V P         V A E
        S GVS          TT G                 S   A  MQA  N YAR V    V   S    NI  DV        D NSN
                                              S        DR                   N               D 210        220        230        240        250        260        270
         |          |          |          |          |          |          |
        PGVSIQSTLPGGTYGAYNGTSMATPHVAGAAALILSKHPTWTNAQVRDRLESTATYLGNSFYYGKGLINVQAAAQ
             NK         S                      N T SS NTK D                     E
                                                DR  NR S
        AGVY Y TN             S                L AS
```

*FIG. 1*

Suppressor mutation of the Met(-60)Thr pro-sequence mutant

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 352 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Bacillus subtilis
        ( B ) STRAIN: 168

( i x ) FEATURE:
        ( A ) NAME/KEY: Region
        ( B ) LOCATION: 1..77
        ( D ) OTHER INFORMATION: /note= "The region from 1 to 77 is a propeptide."

( x i ) SEQUENCE DESCRIPTION: SEQ ID NO:1:

```
Ala Gly Lys Ser Ser Thr Glu Lys Lys Tyr Ile Val Gly Phe Lys Gln
 1               5                  10                  15

Thr Met Ser Ala Met Ser Ser Ala Lys Lys Lys Asp Val Ile Ser Glu
            20                  25                  30

Lys Gly Gly Lys Val Gln Lys Gln Phe Lys Tyr Val Asn Ala Ala Ala
        35                  40                  45

Ala Thr Leu Asp Glu Lys Ala Val Lys Glu Leu Lys Lys Asp Pro Ser
    50                  55                  60

Val Ala Tyr Val Glu Glu Asp His Ile Ala His Glu Tyr Ala Gln Ser
65                  70                  75                  80

Val Pro Tyr Gly Ile Ser Gln Ile Lys Ala Pro Ala Leu His Ser Gln
                    85                  90                  95

Gly Tyr Thr Gly Ser Asn Val Lys Val Ala Val Ile Asp Ser Gly Ile
                100                 105                 110

Asp Ser Ser His Pro Asp Leu Asn Val Arg Gly Gly Ala Ser Phe Val
            115                 120                 125

Pro Ser Glu Thr Asn Pro Tyr Gln Asp Gly Ser Ser His Gly Thr His
    130                 135                 140

Val Ala Gly Thr Ile Ala Ala Leu Asn Asn Ser Ile Gly Val Leu Gly
145                 150                 155                 160

Val Ser Pro Ser Ala Ser Leu Tyr Ala Val Lys Val Leu Asp Ser Thr
                    165                 170                 175

Gly Ser Gly Gln Tyr Ser Trp Ile Ile Asn Gly Ile Glu Trp Ala Ile
                180                 185                 190

Ser Asn Asn Met Asp Val Ile Asn Met Ser Leu Gly Gly Pro Thr Gly
            195                 200                 205

Ser Thr Ala Leu Lys Thr Val Val Asp Lys Ala Val Ser Ser Gly Ile
```

|     |     |     |     | 210 |     |     |     |     | 215 |     |     |     | 220 |     |
|-----|-----|-----|-----|-----|-----|-----|-----|-----|-----|-----|-----|-----|-----|-----|
| Val 225 | Val | Ala | Ala | Ala | Ala 230 | Gly | Asn | Glu | Gly | Ser 235 | Gly | Ser | Thr | Ser 240 |
| Thr | Val | Gly | Tyr | Pro 245 | Ala | Lys | Tyr | Pro | Ser 250 | Thr | Ile | Ala | Val | Gly Ala 255 |
| Val | Asn | Ser | Ser 260 | Asn | Gln | Arg | Ala | Ser 265 | Phe | Ser | Ser | Ala | Gly 270 | Ser Glu |
| Leu | Asp | Val 275 | Met | Ala | Pro | Gly | Val 280 | Ser | Ile | Gln | Ser | Thr 285 | Leu | Pro Gly |
| Gly | Thr 290 | Tyr | Gly | Ala | Tyr | Asn 295 | Gly | Thr | Ser | Met | Ala 300 | Thr | Pro | His Val |
| Ala 305 | Gly | Ala | Ala | Ala | Leu 310 | Ile | Leu | Ser | Lys | His 315 | Pro | Thr | Trp | Thr Asn 320 |
| Ala | Gln | Val | Arg | Asp 325 | Arg | Leu | Glu | Ser | Thr 330 | Ala | Thr | Tyr | Leu | Gly Asn 335 |
| Ser | Phe | Tyr | Tyr 340 | Gly | Lys | Gly | Leu | Ile 345 | Asn | Val | Gln | Ala | Ala 350 | Ala Gln |

(2) INFORMATION FOR SEQ ID NO:2:

(i) SEQUENCE CHARACTERISTICS:
        (A) LENGTH: 352 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Bacillus amyloliquefaciens (ix) FEATURE:
        (A) NAME/KEY: Region
        (B) LOCATION: 1..77
        (D) OTHER INFORMATION: /note= "The region from 1 to 77 is a propeptide."

(xi) SEQUENCE DESCRIPTION: SEQ ID NO:2:

|     |     |     |     |     |     |     |     |     |     |     |     |     |     |     |
|-----|-----|-----|-----|-----|-----|-----|-----|-----|-----|-----|-----|-----|-----|-----|
| Ala 1 | Gly | Lys | Ser | Asn 5 | Gly | Glu | Lys | Lys | Tyr 10 | Ile | Val | Gly | Phe | Lys Gln 15 |
| Thr | Met | Ser | Thr 20 | Met | Ser | Ala | Ala | Lys 25 | Lys | Lys | Asp | Val | Ile 30 | Ser Glu |
| Lys | Gly | Gly 35 | Lys | Val | Gln | Lys | Gln 40 | Phe | Lys | Tyr | Val | Asp 45 | Ala | Ala Ser |
| Ala | Thr 50 | Leu | Asn | Glu | Lys | Ala 55 | Val | Lys | Glu | Leu | Lys 60 | Lys | Asp | Pro Ser |
| Val 65 | Ala | Tyr | Val | Glu | Glu 70 | Asp | His | Val | Ala | His 75 | Ala | Tyr | Ala | Gln Ser 80 |
| Val | Pro | Tyr | Gly | Val 85 | Ser | Gln | Ile | Lys | Ala 90 | Pro | Ala | Leu | His | Ser Gln 95 |
| Gly | Tyr | Thr | Gly 100 | Ser | Asn | Val | Lys | Val 105 | Ala | Val | Ile | Asp | Ser 110 | Gly Ile |
| Asp | Ser | Ser 115 | His | Pro | Asp | Leu | Lys 120 | Val | Ala | Gly | Gly | Ala 125 | Ser | Met Val |
| Pro | Ser 130 | Glu | Thr | Asn | Pro | Phe 135 | Gln | Asp | Asn | Asn | Ser 140 | His | Gly | Thr His |
| Val 145 | Ala | Gly | Thr | Val | Ala 150 | Ala | Leu | Asn | Asn | Ser 155 | Ile | Gly | Val | Leu Gly 160 |

```
Val  Ala  Pro  Ser  Ala  Ser  Leu  Tyr  Ala  Val  Lys  Val  Leu  Gly  Ala  Asp
               165                      170                     175

Gly  Ser  Gly  Gln  Tyr  Ser  Trp  Ile  Ile  Asn  Gly  Ile  Glu  Trp  Ala  Ile
               180                      185                     190

Ala  Asn  Asn  Met  Asp  Val  Ile  Asn  Met  Ser  Leu  Gly  Gly  Pro  Ser  Gly
          195                      200                     205

Ser  Ala  Ala  Leu  Lys  Ala  Ala  Val  Asp  Lys  Ala  Val  Ala  Ser  Gly  Val
     210                      215                     220

Val  Val  Val  Ala  Ala  Ala  Gly  Asn  Glu  Gly  Thr  Ser  Gly  Ser  Ser  Ser
225                      230                     235                          240

Thr  Val  Gly  Tyr  Pro  Gly  Lys  Tyr  Pro  Ser  Val  Ile  Ala  Val  Gly  Ala
               245                      250                     255

Val  Asp  Ser  Ser  Asn  Gln  Arg  Ala  Ser  Phe  Ser  Ser  Val  Gly  Pro  Glu
               260                      265                     270

Leu  Asp  Val  Met  Ala  Pro  Gly  Val  Ser  Ile  Gln  Ser  Thr  Leu  Pro  Gly
          275                      280                     285

Asn  Lys  Tyr  Gly  Ala  Tyr  Asn  Gly  Thr  Ser  Met  Ala  Ser  Pro  His  Val
     290                      295                     300

Ala  Gly  Ala  Ala  Ala  Leu  Ile  Leu  Ser  Lys  His  Pro  Asn  Trp  Thr  Asn
305                      310                     315                          320

Thr  Gln  Val  Arg  Ser  Ser  Leu  Glu  Asn  Thr  Thr  Thr  Lys  Leu  Gly  Asp
               325                      330                     335

Ser  Phe  Tyr  Tyr  Gly  Lys  Gly  Leu  Ile  Asn  Val  Gln  Ala  Ala  Ala  Gln
               340                      345                     350
```

( 2 ) INFORMATION FOR SEQ ID NO:3:

( i ) SEQUENCE CHARACTERISTICS:
        ( A ) LENGTH: 352 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Bacillus amylosacchariticus ( i x ) FEATURE:
        ( A ) NAME/KEY: Region
        ( B ) LOCATION: 1..77
        ( D ) OTHER INFORMATION: /note= "The region from 1 to 77 is
            a propeptide."

( x i ) SEQUENCE DESCRIPTION: SEQ ID NO:3:

```
Ala  Gly  Lys  Ser  Asn  Gly  Glu  Lys  Lys  Tyr  Ile  Val  Gly  Phe  Lys  Gln
 1              5                       10                      15

Thr  Met  Ser  Thr  Met  Ser  Ala  Ala  Lys  Lys  Asp  Val  Ile  Ser  Glu
               20                       25                      30

Lys  Gly  Gly  Lys  Val  Gln  Lys  Gln  Phe  Lys  Tyr  Val  Asp  Ala  Ala  Ser
               35                       40                      45

Ala  Thr  Leu  Asn  Glu  Lys  Ala  Val  Lys  Glu  Leu  Lys  Lys  Asp  Pro  Ser
     50                       55                      60

Val  Ala  Tyr  Val  Glu  Glu  Asp  His  Val  Ala  His  Ala  Tyr  Ala  Gln  Ser
65                        70                      75                          80

Val  Pro  Tyr  Gly  Val  Ser  Gln  Ile  Lys  Ala  Pro  Ala  Leu  His  Ser  Gln
               85                       90                      95
```

| | | | | | | | | | | | | | | | |
|---|---|---|---|---|---|---|---|---|---|---|---|---|---|---|---|
| Gly | Tyr | Thr | Gly<br>100 | Ser | Asn | Val | Lys | Val<br>105 | Ala | Val | Ile | Asp | Ser<br>110 | Gly | Ile |
| Asp | Ser | Ser<br>115 | His | Pro | Asp | Leu | Asn<br>120 | Val | Arg | Gly | Gly | Ala<br>125 | Ser | Phe | Val |
| Pro | Ser | Glu<br>130 | Thr | Asn | Pro | Tyr<br>135 | Gln | Asp | Gly | Asn | Ser<br>140 | His | Gly | Thr | His |
| Val<br>145 | Ala | Gly | Thr | Val | Ala<br>150 | Ala | Leu | Asn | Asn | Ser<br>155 | Ile | Gly | Val | Leu | Gly<br>160 |
| Val | Ala | Pro | Ser | Ala<br>165 | Ser | Leu | Tyr | Ala | Val<br>170 | Lys | Val | Leu | Asp | Ser<br>175 | Thr |
| Gly | Ser | Gly | Gln<br>180 | Tyr | Ser | Trp | Ile | Ile<br>185 | Asn | Gly | Ile | Glu | Trp<br>190 | Ala | Ile |
| Ser | Asn | Asn<br>195 | Met | Asp | Val | Ile | Asn<br>200 | Met | Ser | Leu | Gly | Gly<br>205 | Pro | Ser | Gly |
| Ser | Thr<br>210 | Ala | Leu | Lys | Thr<br>215 | Val | Asp | Lys | Ala | Val<br>220 | Ser | Ser | Gly | Ser |
| Ile<br>225 | Val | Ala | Ala | Ala | Ala<br>230 | Gly | Asn | Glu | Gly | Ser<br>235 | Ser | Gly | Ser | Ser | Ser<br>240 |
| Thr | Val | Gly | Tyr | Pro<br>245 | Ala | Lys | Tyr | Pro | Ser<br>250 | Val | Ile | Ala | Val<br>255 | Gly | Ala |
| Val | Asn | Ser | Ser<br>260 | Asn | Gln | Arg | Ala | Ser<br>265 | Phe | Ser | Ser | Val<br>270 | Gly | Ser | Glu |
| Leu | Asp | Val<br>275 | Met | Ala | Pro | Gly | Val<br>280 | Ser | Ile | Gln | Ser | Thr<br>285 | Leu | Pro | Gly |
| Gly | Thr<br>290 | Tyr | Gly | Ala | Tyr | Asn<br>295 | Gly | Thr | Ser | Met | Ala<br>300 | Thr | Pro | His | Val |
| Ala<br>305 | Gly | Ala | Ala | Ala | Leu<br>310 | Ile | Leu | Ser | Lys | His<br>315 | Pro | Thr | Trp | Thr | Asn<br>320 |
| Ala | Gln | Val | Arg | Asp<br>325 | Arg | Leu | Glu | Ser | Thr<br>330 | Ala | Thr | Tyr | Leu | Gly<br>335 | Asp |
| Ser | Phe | Tyr | Tyr<br>340 | Gly | Lys | Gly | Leu | Ile<br>345 | Asn | Val | Gln | Ala | Ala<br>350 | Ala | Gln |

(2) INFORMATION FOR SEQ ID NO:4:

(i) SEQUENCE CHARACTERISTICS:
        (A) LENGTH: 350 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Bacillus licheniformis (ix) FEATURE:
        (A) NAME/KEY: Region
        (B) LOCATION: 1..76
        (D) OTHER INFORMATION: /note= "The region from 1 to 76 is a propeptide."

(xi) SEQUENCE DESCRIPTION: SEQ ID NO:4:

| | | | | | | | | | | | | | | | |
|---|---|---|---|---|---|---|---|---|---|---|---|---|---|---|---|
| Ala<br>1 | Gln | Pro | Ala | Lys<br>5 | Asn | Val | Glu | Lys | Asp<br>10 | Tyr | Ile | Val | Gly | Phe<br>15 | Lys |
| Ser | Gly | Val | Lys<br>20 | Thr | Ala | Ser | Val | Lys<br>25 | Lys | Asp | Ile | Ile | Lys<br>30 | Glu | Ser |
| Gly | Gly | Lys | Val | Asp | Lys | Gln | Phe | Arg | Ile | Ile | Asn | Ala | Ala | Lys | Ala |

```
                    35                        40                        45

Lys  Leu  Asp  Lys  Glu  Ala  Leu  Lys  Glu  Val  Lys  Asn  Asp  Pro  Asp  Val
             50                      55                      60

Ala  Tyr  Val  Glu  Glu  Asp  His  Val  Ala  His  Ala  Leu  Ala  Gln  Thr  Val
        65                      70                      75                           80

Pro  Tyr  Gly  Ile  Pro  Leu  Ile  Lys  Ala  Asp  Lys  Val  Gln  Ala  Gln  Gly
                            85                      90                      95

Phe  Lys  Gly  Ala  Asn  Val  Lys  Val  Ala  Val  Leu  Asp  Thr  Gly  Ile  Gln
                       100                     105                     110

Ala  Ser  His  Pro  Asp  Leu  Asn  Val  Val  Gly  Gly  Ala  Ser  Phe  Val  Ala
                       115                     120                     125

Gly  Glu  Ala  Tyr  Asn  Thr  Asp  Gly  Asn  Gly  His  Gly  Thr  His  Val  Ala
                  130                     135                     140

Gly  Thr  Val  Ala  Ala  Leu  Asp  Asn  Thr  Thr  Gly  Val  Leu  Gly  Val  Ala
        145                     150                     155                          160

Pro  Ser  Val  Ser  Leu  Tyr  Ala  Val  Lys  Val  Leu  Asn  Ser  Ser  Gly  Ser
                            165                     170                     175

Gly  Thr  Tyr  Ser  Gly  Ile  Val  Ser  Gly  Ile  Glu  Trp  Ala  Thr  Thr  Asn
                       180                     185                     190

Gly  Met  Asp  Val  Ile  Asn  Met  Ser  Leu  Gly  Gly  Pro  Ser  Gly  Ser  Thr
                  195                     200                     205

Ala  Met  Lys  Gln  Ala  Val  Asp  Asn  Ala  Tyr  Ala  Arg  Gly  Val  Val  Val
                  210                     215                     220

Val  Ala  Ala  Ala  Gly  Asn  Ser  Gly  Ser  Ser  Gly  Asn  Thr  Asn  Thr  Ile
        225                     230                     235                          240

Gly  Tyr  Pro  Ala  Lys  Tyr  Asp  Ser  Val  Ile  Ala  Val  Gly  Ala  Val  Asp
                            245                     250                     255

Ser  Asn  Ser  Asn  Arg  Ala  Ser  Phe  Ser  Ser  Val  Gly  Ala  Glu  Leu  Glu
                       260                     265                     270

Val  Met  Ala  Pro  Gly  Ala  Gly  Val  Tyr  Ser  Thr  Tyr  Pro  Thr  Ser  Thr
                  275                     280                     285

Tyr  Ala  Thr  Leu  Asn  Gly  Thr  Ser  Met  Ala  Ser  Pro  His  Val  Ala  Gly
             290                     295                     300

Ala  Ala  Ala  Leu  Ile  Leu  Ser  Lys  His  Pro  Asn  Leu  Ser  Ala  Ser  Gln
        305                     310                     315                          320

Val  Arg  Asn  Arg  Leu  Ser  Ser  Thr  Ala  Thr  Tyr  Leu  Gly  Ser  Ser  Phe
                            325                     330                     335

Tyr  Tyr  Gly  Lys  Gly  Leu  Ile  Asn  Val  Glu  Ala  Ala  Ala  Gln
                       340                     345                     350
```

( 2 ) INFORMATION FOR SEQ ID NO:5:

( i ) SEQUENCE CHARACTERISTICS:
        ( A ) LENGTH: 77 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Bacillus subtilis
        ( B ) STRAIN: 168

( i x ) FEATURE:
        ( A ) NAME/KEY: Region
        ( B ) LOCATION: 1..77

-continued (D) OTHER INFORMATION: /note= "The region from 1 to 77 is a propeptide."

(ix) FEATURE:
 (A) NAME/KEY: Region
 (B) LOCATION: 2
 (D) OTHER INFORMATION: /note= "Amino acid residue 2 is glycine or valine."

(ix) FEATURE:
 (A) NAME/KEY: Region
 (B) LOCATION: 3
 (D) OTHER INFORMATION: /note= "Amino acid residue 3 is lysine, arginine, cysteine, or serine."

(ix) FEATURE:
 (A) NAME/KEY: Region
 (B) LOCATION: 11
 (D) OTHER INFORMATION: /note= "Amino acid residue 11 is isoleucine or cysteine."

(ix) FEATURE:
 (A) NAME/KEY: Region
 (B) LOCATION: 12
 (D) OTHER INFORMATION: /note= "Amino acid residue 12 is valine or threonine."

(ix) FEATURE:
 (A) NAME/KEY: Region
 (B) LOCATION: 13
 (D) OTHER INFORMATION: /note= "Amino acid residue 13 is glycine or alanine."

(ix) FEATURE:
 (A) NAME/KEY: Region
 (B) LOCATION: 19
 (D) OTHER INFORMATION: /note= "Amino acid residue 19 is serine or threonine."

(ix) FEATURE:
 (A) NAME/KEY: Region
 (B) LOCATION: 30
 (D) OTHER INFORMATION: /note= "Amino acid residue 30 is isoleucine, threonine, serine, or valine."

(ix) FEATURE:
 (A) NAME/KEY: Region
 (B) LOCATION: 33
 (D) OTHER INFORMATION: /note= "Amino acid residue 33 is lysine or glutamic acid."

(ix) FEATURE:
 (A) NAME/KEY: Region
 (B) LOCATION: 34
 (D) OTHER INFORMATION: /note= "Amino acid residue 34 is glycine or aspartic acid."

(ix) FEATURE:
 (A) NAME/KEY: Region
 (B) LOCATION: 37
 (D) OTHER INFORMATION: /note= "Amino acid residue 37 is valine or alanine."

(ix) FEATURE:
 (A) NAME/KEY: Region
 (B) LOCATION: 42
 (D) OTHER INFORMATION: /note= "Amino acid residue 42 is lycine or glutamic acid."

(ix) FEATURE:
 (A) NAME/KEY: Region
 (B) LOCATION: 44
 (D) OTHER INFORMATION: /note= "Amino acid residue 44 is valine, arginine, or isoleucine."

(ix) FEATURE:
 (A) NAME/KEY: Region
 (B) LOCATION: 45
 (D) OTHER INFORMATION: /note= "Amino acid residue 45 is asparagine or serine."

( i x ) FEATURE:
          ( A ) NAME/KEY: Region
          ( B ) LOCATION: 46
          ( D ) OTHER INFORMATION: /note= "Amino acid residue 46 is
                  alanine or threonine."

( i x ) FEATURE:
          ( A ) NAME/KEY: Region
          ( B ) LOCATION: 47
          ( D ) OTHER INFORMATION: /note= "Amino acid residue 47 is
                  alanine or threonine."

( i x ) FEATURE:
          ( A ) NAME/KEY: Region
          ( B ) LOCATION: 48
          ( D ) OTHER INFORMATION: /note= "Amino acid residue 48 is
                  alanine or threonine."

( i x ) FEATURE:
          ( A ) NAME/KEY: Region
          ( B ) LOCATION: 49
          ( D ) OTHER INFORMATION: /note= "Amino acid residue 49 is
                  alanine or threonine."

( i x ) FEATURE:
          ( A ) NAME/KEY: Region
          ( B ) LOCATION: 63
          ( D ) OTHER INFORMATION: /note= "Amino acid residue 63 is
                  proline or leucine."

( i x ) FEATURE:
          ( A ) NAME/KEY: Region
          ( B ) LOCATION: 65
          ( D ) OTHER INFORMATION: /note= "Amino acid residue 65 is
                  valine or alanine."

( i x ) FEATURE:
          ( A ) NAME/KEY: Region
          ( B ) LOCATION: 71
          ( D ) OTHER INFORMATION: /note= "Amino acid residue 71 is
                  aspartic acid or asparagine."

( x i ) SEQUENCE DESCRIPTION: SEQ ID NO:5:

Ala  Xaa  Xaa  Ser  Ser  Thr  Glu  Lys  Lys  Tyr  Xaa  Xaa  Xaa  Phe  Lys  Gln
 1               5                         10                          15

Thr  Met  Xaa  Ala  Met  Ser  Ser  Ala  Lys  Lys  Lys  Asp  Val  Xaa  Ser  Glu
              20                        25                       30

Xaa  Xaa  Gly  Lys  Xaa  Gln  Lys  Gln  Phe  Xaa  Tyr  Xaa  Xaa  Xaa  Xaa  Xaa
          35                       40                       45

Xaa  Thr  Leu  Asp  Glu  Lys  Ala  Val  Lys  Glu  Leu  Lys  Lys  Asp  Xaa  Ser
     50                       55                       60

Xaa  Ala  Tyr  Val  Glu  Glu  Xaa  His  Ile  Ala  His  Glu  Tyr
 65                       70                  75

( 2 ) INFORMATION FOR SEQ ID NO:6:

( i ) SEQUENCE CHARACTERISTICS:
            ( A ) LENGTH: 352 amino acids
            ( B ) TYPE: amino acid
            ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
            ( A ) ORGANISM: Bacillus subtilis
            ( B ) STRAIN: 168

( i x ) FEATURE:
            ( A ) NAME/KEY: Region (B) LOCATION: 1..77
(D) OTHER INFORMATION: /note= "The region from 1 to 77 is a propeptide."

(ix) FEATURE:
(A) NAME/KEY: Region
(B) LOCATION: 18
(D) OTHER INFORMATION: /note= "Amino acid residue 18 is methionine or threonine."

(ix) FEATURE:
(A) NAME/KEY: Region
(B) LOCATION: 265
(D) OTHER INFORMATION: /note= "Amino acid residue 265 is serine or leucine."

(xi) SEQUENCE DESCRIPTION: SEQ ID NO:6:

| | | | | | | | | | | | | | | |
|---|---|---|---|---|---|---|---|---|---|---|---|---|---|---|
| Ala 1 | Gly | Lys | Ser | Ser 5 | Thr | Glu | Lys | Lys | Tyr 10 | Ile | Val | Gly | Phe | Lys 15 | Gln |
| Thr | Xaa | Ser | Ala 20 | Met | Ser | Ser | Ala | Lys 25 | Lys | Lys | Asp | Val | Ile 30 | Ser | Glu |
| Lys | Gly | Gly 35 | Lys | Val | Gln | Lys | Gln 40 | Phe | Lys | Tyr | Val | Asn 45 | Ala | Ala | Ala |
| Ala | Thr 50 | Leu | Asp | Glu | Lys | Ala 55 | Val | Lys | Glu | Leu | Lys 60 | Lys | Asp | Pro | Ser |
| Val 65 | Ala | Tyr | Val | Glu | Glu 70 | Asp | His | Ile | Ala | His 75 | Glu | Tyr | Ala | Gln | Ser 80 |
| Val | Pro | Tyr | Gly | Ile 85 | Ser | Gln | Ile | Lys | Ala 90 | Pro | Ala | Leu | His | Ser 95 | Gln |
| Gly | Tyr | Thr | Gly 100 | Ser | Asn | Val | Lys | Val 105 | Ala | Val | Ile | Asp | Ser 110 | Gly | Ile |
| Asp | Ser | Ser 115 | His | Pro | Asp | Leu | Asn 120 | Val | Arg | Gly | Gly | Ala 125 | Ser | Phe | Val |
| Pro | Ser 130 | Glu | Thr | Asn | Pro | Tyr 135 | Gln | Asp | Gly | Ser | Ser 140 | His | Gly | Thr | His |
| Val 145 | Ala | Gly | Thr | Ile | Ala 150 | Ala | Leu | Asn | Asn | Ser 155 | Ile | Gly | Val | Leu | Gly 160 |
| Val | Ser | Pro | Ser | Ala 165 | Ser | Leu | Tyr | Ala | Val 170 | Lys | Val | Leu | Asp | Ser 175 | Thr |
| Gly | Ser | Gly | Gln 180 | Tyr | Ser | Trp | Ile | Ile 185 | Asn | Gly | Ile | Glu | Trp 190 | Ala | Ile |
| Ser | Asn | Asn 195 | Met | Asp | Val | Ile | Asn 200 | Met | Ser | Leu | Gly | Gly 205 | Pro | Thr | Gly |
| Ser | Thr 210 | Ala | Leu | Lys | Thr | Val 215 | Val | Asp | Lys | Ala | Val 220 | Ser | Ser | Gly | Ile |
| Val 225 | Val | Ala | Ala | Ala | Ala 230 | Gly | Asn | Glu | Gly | Ser 235 | Ser | Gly | Ser | Thr | Ser 240 |
| Thr | Val | Gly | Tyr | Pro 245 | Ala | Lys | Tyr | Pro | Ser 250 | Thr | Ile | Ala | Val | Gly 255 | Ala |
| Val | Asn | Ser | Ser | Asn 260 | Gln | Arg | Ala | Xaa 265 | Phe | Ser | Ser | Ala | Gly 270 | Ser | Glu |
| Leu | Asp | Val 275 | Met | Ala | Pro | Gly | Val 280 | Ser | Ile | Gln | Ser | Thr 285 | Leu | Pro | Gly |
| Gly | Thr 290 | Tyr | Gly | Ala | Tyr | Asn 295 | Gly | Thr | Ser | Met | Ala 300 | Thr | Pro | His | Val |
| Ala 305 | Gly | Ala | Ala | Ala | Leu 310 | Ile | Leu | Ser | Lys | His 315 | Pro | Thr | Trp | Thr | Asn 320 |
| Ala | Gln | Val | Arg | Asp 325 | Arg | Leu | Glu | Ser | Thr 330 | Ala | Thr | Tyr | Leu | Gly 335 | Asn |

-continued

```
Ser Phe Tyr Tyr Gly Lys Gly Leu Ile Asn Val Gln Ala Ala Ala Gln
                340                 345                 350
```

(2) INFORMATION FOR SEQ ID NO:7:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:7:

```
Ala Ala Ala Ala Thr Leu
 1               5
```

(2) INFORMATION FOR SEQ ID NO:8:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:8:

```
Val Val Val Val Ser Ile
 1               5
```

(2) INFORMATION FOR SEQ ID NO:9:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:9:

```
Tyr Val Asn Ala Ala Ala Ala Thr Leu
 1               5
```

(2) INFORMATION FOR SEQ ID NO:10:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:10:

```
Tyr Ile Val Gly Phe
 1               5
```

(2) INFORMATION FOR SEQ ID NO:11:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:11:

```
Val Ala Tyr Val
 1
```

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:12:

```
CCATGATTAC GGATTCAC                                                              18
```

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
TGGGTTTGTT TCAGAAGG                                                              18
```

PROTEIN ACTIVATION

This is a continuation-in-part of pending U.S. patent application Ser. No. 07/346,552, filed May 2, 1989, entitled "Production of Biologically Active Polypeptides by Treatment with an Exogenous Peptide Sequence", incorporated herein by reference now U.S. Pat. No. 5,191,063.

FIELD OF THE INVENTION

The invention relates to biochemically active proteins. The invention also relates to a method of broad application for biochemically activating biochemically inactive proteins.

BACKGROUND OF THE INVENTION

The biological activity of proteins is dependent on the proteins assuming their proper three dimensional conformation. The proper conformation determines the activity and/or stability of the proteins. Most proteins possess all the information necessary for folding into the active conformation stored within the sequence of the polypeptide itself. Proteins of this type when denatured by agents known to denature proteins, such as temperatures above or below the physiological temperature range or chemicals such as urea or guanidine hydrochloride, are capable of refolding to their original biochemically active conformation up removal of the denaturant.

However, other proteins are unable on their own to refold properly once they are denatured, even when the proteins are removed from the condition or chemical which caused denaturation. This is the case for instance of subtilisin, a-lyric proteases and carboxypeptidase.

Within the group of proteins which cannot refold properly into a biochemically active conformation are certain enzymes. Enzymes have been studied quite extensively to determine correlation between the three dimensional structure of the enzymes and their activity or stability. However, the invention as described herein below is not limited to enzymes but deals broadly with other proteins.

In the field of genetic engineering, proteins encoded by appropriate genetic elements can be produced and expressed in host cell systems. Many non-bacterial genes that are engineered in an appropriate expression system in bacterial cells express non-bacterial gene products that are quite susceptible to the host cell degrative proteolytic enzymes. These foreign proteins are thus quite labile when synthesized in such bacterial cells. Thus, instead of expressing a biochemically active protein, the product has decreased biological activity or is not even biochemically active. This of course is undesirable. One way to address this problem is to express the protein of interest as a fused protein which contains a portion of a bacterial protein fused to the eukaryote protein of interest. However, fusion proteins when produced in higher than physiologically nominal amounts, tend to form insoluble aggregates either in the host cell or upon cell lysis. It is a cumbersome procedure to obtain the physiologically active protein from the aggregates. One procedure to dissociate the aggregate to release the desired mature protein which, however, is then biochemically inactive. There is a need for reactivating such proteins. There are also many other situations where it is desired to reactivate proteins that are inactivated physiologically due to various environmental factors to which they are exposed.

BACKGROUND ART

The status of basic research into protein folding and attempts to clarify this phenomenon have been reviewed in "Protein Folding, Deciphering the Second Half of the Genetic Code", edited by Lila M. Gierasch and Jonathan King, American Association for the Advancement of Science, 1990. The Preface of this book notes that it is still not possible at this time to predict reliably or even to understand how the sequence of the amino acids determine the spatial organization of the polypeptide chain. The Preface also notes that the rules through which the amino acid sequence determines the folding of the polypeptide represents as the editors note, "an undeciphered aspect of the genetic code". The editors list several reasons for the "increasingly urgent need to break this part of the code".

This invention contributes in a fundamental way to the understanding of the phenomena of protein folding from a biochemically inactive to a biochemically active conformation.

The invention specially deals with polypeptides which normally, but not necessarily, are expressed in precursor form containing a pro-sequence which, without their natural pro-sequence are biochemically inactive and which in accordance with the invention are made to fold into a biochemically active conformation through an activating peptide-mediated folding.

In "Up the Kinetic Pathway", Nature, 356, 192–193 (1992), T. E. Creighton, discusses the kinetics of protein folding and notes that the mature forms of bacterial proteases can be refolded in the presence of added pro-segment.

In "The α-lytic Protease Pro-Region Does Not Require a Physical Linkage to Activate the Protease Domain In Vivo", J. L. Silen and D. A. Agard, in Nature, 341, 1320–1325 (1989), report experiments with α-lytic protease which indicate that the pro-region (166 amino acids long), which is covalently attached to, but only transiently associated with the protease domain, is necessary for correct folding of the enzyme.

In "Analysis of Pre-pro-α-lytic Protease Expression in E. coli Reveals that the Pro Region is Required for Activity", Silen J. L. et al. in J. Bact., 171, 1320–1325 (1989) confirm their earlier above-referred to report.

Roy et al., report studies on the "Investigation of a Possible Role of the Amino-Terminal Pro-Region of Proopiomelanocortin in its Processing and Targeting to Secretory Granules", in Molecular and Cellular Endocrinology, 82, 237–250 (1991).

Wakefield et al., report studies on the "Addition of a C-Terminal Extension Sequence to Transforming Growth Factor-β1 Interferes with Biosynthetic Processing and Abolishes Biological Activity", in Growth Factors, 5, 243–253 (1991).

Norman et al., report studies on the "Stable Expression, Secretion, and Characterization of Active Human Renin in Mammalian Cells", in Mol. Pharmacol., 41, 53–59 (1992).

Lin et al., report studies on the "Synthesis, Purification, and Active Site Mutagenesis of Recombinant Porcine Pepsinogen", in The Journal of Biological Chemistry, 264, (8), pages 4482–4489 (1989) and also reports studies with porcine pepsinogen, an aspartic protease.

Winther et al., report that carboxypeptidase when unfolded in guanidine HCL has been shown to refold only in the presence of its pro-peptide. Proc. Natl. Acad. Sci. U.S.A., 88, 9330–9334 (1991).

SUMMARY OF THE INVENTION

The invention relates to the practice and application of a new general and fundamental concept. The invention provides a system for biochemically activating a biochemically inactive polypeptide into a biochemically active conformation by means of what is called herein an "activating" peptide which guides or assists in the folding of the inactive polypeptide into a physiologically active conformation.

From an overall view, the invention relates to a first method for identifying at least one functional domain in a native pro-sequence of a target polypeptide (if such polypeptide has a pro-sequence) which is essential to the folding of an inactive (or denatured) target polypeptide into a biochemically active conformation. The second method of the invention relates to a folding reaction of the target mature inactive (or denatured) polypeptide with a tailor-made activating peptide which contains one or more identified functional domains in which method the folding of the inactive polypeptide into a biochemically active conformation occurs by an intermolecular reaction with the activating peptide. In this method, the activating peptide can be synthetic or made by recombinant DNA methods.

As described hereinafter, the first method of the invention (identification method) involves the construction of genetically engineered pro-sequences of a target polypeptide which normally, but not always, is expressed in precursor form containing a pro-sequence and fusing these bio-engineered pro-sequences to respective bio-engineered mature target polypeptides. The pro-sequences are constructed to contain random mutations some of which inhibit the folding reaction of the target peptide. The mature portion of the target polypeptide is then also bio-engineered to contain random mutations which suppress the inhibitory effect of the pro-sequence mutation, so that the folding activity is restored. In this manner and by testing for the biological activity of the target polypeptide, at least one functional domain in the pro-sequence which is essential to promote folding of the polypeptide is identified. Thus, the reaction of the identification method is an intramolecular reaction as contrasted with the activation method describes below, which occurs via an intermolecular reaction.

The nature of the identification method of the invention allows for identification of the proteins' functional domain regardless of their polarity. Thus, the identification method is applicable regardless of whether the functional domains are hydrophobic or hydrophilic. The method has been illustrated but not limited to, identifying hydrophobic domains.

For use in the second method of the invention (activation method), an appropriate peptide (activating peptide) is constructed which contains at least one of the identified functional domains of the native pro-sequence effective to activate the target inactive mature polypeptide. The activating peptide is reacted in vitro with the target polypeptide in a medium which favors their interactions, if the synthetic peptide and the mature protein react by hydrophobic interaction, a medium of high ionic strength will promote folding of the target polypeptide into a biochemically active configuration.

The invention is broadly conceived and contemplates activating any biochemically inactive (or inadequately active) polypeptide. The invention is applicable irrespective of whether the polypeptide is known to date or yet to be discovered. The invention is also applicable irrespective of what is known to date about the active conformation of polypeptides, its folding (and unfolding) mechanism and of any related aspects. The invention is also applicable irrespective of what is known about the need for a pro-sequence (in the strict definition of pro-sequence) or of an equivalent sequence for folding into a biochemically active conformation. The invention has involved the discovery of such fundamental principles that its broadest contribution to the field of protein chemistry may be expected to open wide vistas into the future.

The invention also relates to synthetic peptides which contain at least one functional domain to activate the polypeptide. The invention further relates to the biochemically active mature polypeptides obtained by the activation method of invention.

In the context of this invention, the mature polypeptide is defined as the polypeptide molecule which does not contain its pro-sequence or an equivalent sequence (or pre- pro-sequence). The term "mature polypeptide" refers to both the biochemically active peptide that is properly folded and to the inactive peptide which is denatured.

The term "biochemically active" is intended to be understood in its broadest possible meaning and include physiologically, "biologically", etc.

The proteins of the invention are folded properly when they gave regained their biochemical activity. This of course will vary for each individual protein folded but some generalizations can be made. For example, proteases can be assayed for their ability to degrade a substrate peptide like casein or albumin. Hormone and growth factors can be tested by assaying for their interaction with the appropriate receptor molecules. All such assays are known.

In the context of this invention reference will be made to "native pro-sequence" or "native pro-peptide" as the sequence of nucleotides or amino acids which is formed naturally in the precursor of the mature polypeptide. For instance, the pro-sequences of the various species of insulins of 30 to 35 amino acid residues or the pro-sequence of 77 residues of subtilisin.

"Mutated pro-sequence" or "mutated pro-peptide" refers to that amino acid sequence obtained by genetic engineering by what is called herein the "identification method".

The nucleotide sequences or peptide which contain functional domains which promote the folding of the mature polypeptide into a biochemically active form is referred to as "activating sequence" or "activating peptide" more frequently. Such peptide is also often referred to as "tailor-made" because it is constructed to contain one or more domains especially adapted to activate a particular polypeptide (target peptide) which is to be activated. The tailor-made sequence can be generated by genetic engineering or by synthetic methods. When the activating peptide contains one or more functional domains necessary to promote the folding of the target polypeptide and does not contain other unnecessary areas, the activating peptide is likely to be of shorter length i.e. contain less amino acid residues than the native pro-peptide. The activating peptide thus may be shorter, of the same length or longer than the native pro-peptide depending on whether the objective of one skilled in the art. It is desired to insert other amino acids or other residues in the sequence, such added amino acids or other residues should not adversely affect the function of the functional domain(s).

The activating peptide need not contain any amino acid residues identical to the native pro-sequence (when the peptide has a pro-sequence), but to be active in the folding process, it should contain at least functional equivalents of the native pro-sequence residues. For example, the functional domains of the subtilisin pro-sequence are hydrophobic, e.g., ala-ala-ala-ala-thr-leu (SEQ. ID NO.7). A sequence which shows no identity with this domain but retains hydrophobic character can be the following: val-valval-val-ser-ile (SEQ. ID NO.8). This peptide may be functional on the basis of its biochemical properties even though the primary sequence is different.

Synthetic peptides are commonly no longer than approximately 25 residues in length. This is due to limits of the synthetic procedures in use at this time. If activating peptides of longer than approximately 25 residues are desired, they would best be made by recombinant technology. This involves expressing the DNA sequence encoding the propeptide (with or without mutations) in a suitable host and isolating the desired peptide. Also, DNA sequences can be made that code for any combination of amino acids desired. These synthetic DNA sequences will then be ligated into an expression vector and expressed in a suitable host cell. Thus, a consideration for deciding if an activating peptide is best made by synthetic or recombinant means is the length and the nature of amino acids of the peptide itself.

It has been established with respect to certain peptides that the pro-peptide is essential for formation of the active conformation of the mature peptide, but is not required for its biological function. In accordance with the invention, as is described hereinafter in greater detail, it is not necessary that the mature peptide in its entirety becomes physiologically active. It is within the scope of the invention that a proportion, but not necessarily all of the peptide molecules and/or a portion of any single peptide molecules be so folded by the mediating action of the activating peptide that the biochemical activity of the mature peptide be increased from the level it was before being reacted with the activating peptide. The pro-peptide does not function as a catalyst, but rather as a molecule capable of folding one molecule of the inactive mature peptide (partially or completely) of the peptide into the mature peptide.

In studies with subtilisin (but not limited thereto), pro-peptides which are synthetic as opposed to the native pro-sequence, have been shown to contribute to the folding of the peptide to an active conformation by an intermolecular reaction. The amino acid constitution and/or sequence of the amino acid residues of the activating peptide need not be the same as that of the native pro-sequence. It is generally sufficient that it be in part the same as that of the native pro-sequence in that it contains one or more of the identified functional domains to cause the inactive polypeptide to be activated biochemically.

The identification method can be so conducted to determine one or more functional domains responsible for folding the inactive polypeptide into a biochemically active conformation. Substitutions of functionally equivalent amino acids can be performed in the identified domain(s) and the resulting peptide tested in accordance with the identification method. Peptides can thus be made which are still effective to activate the polypeptide but contain no amino acid residue(s) which is identical to that of the native pro-sequence.

In studies in conjunction with the identification method specific regions of a pro-peptide have been identified which appear to contribute to direct the folding of the mature sequence into a biochemically active form. In a model that was tested, these regions are constituted of hydrophobic amino acids residues. Further, it has also been found at least in the case of subtilisins, that the proper refolding is promoted by the presence of hydrophobic amino acid residues in the mature domain of the polypeptide which may be located near or at the active site of the polypeptide. As described hereinafter, the pro-peptide may function as a competitive inhibitor of the enzyme activity when the peptide is properly folded and biochemically active. Further, it has been observed as described below, that the electric charge distribution of the pro -peptide and of the mature peptide domains are very different and that the surface charge of the polypeptide is very uneven. The surface of the region where the substrate binding site is located contains few hydrophilic charges; instead this region is covered by hydrophobic residues. Thus, it is not unlikely that the interaction of the pro-peptide with the physiologically inactive mature polypeptide which is to be activated may be such that the highly charged pro-peptide may have a tendency to cover the hydrophobic surface of the mature polypeptide and that the pro-peptide may interact with or near an active site of the mature polypeptide. This complementation between hydrophobic groups in the pro-peptide and in the mature polypeptide appears to contribute to the proper folding of the inactive mature polypeptide into a physiologically active conformation.

In accordance with the invention, a better understanding has been gained in the mechanism of the folding or refolding of a mature polypeptide into a physiological active conformation. It has been found that when certain amino acid substitution mutations were made in the amino acid constituents of a pro-peptide no mature biochemically active polypeptide was recovered. The mutations inhibited the folding. When a suppressor of the inhibitory activity of the mutation was introduced into the nucleotide region encoding the mature region of the polypeptide resulting in an amino acid substitution in the encoded mature protein, the folding capability of the polypeptide was restored. Thus, a selective nucleotide mutation in the mature sequence is capable of suppressing the inhibitory effect of nucleotide mutations in the pro-peptide sequence. The mutations in the pro-peptide have been observed to occur with high frequency within the hydrophobic region of the pro-peptide. Thus, it appears that the pro-peptide contains select functional domains which interact with specific regions of the mature region of the polypeptide to promote the refolding process.

In accordance with the identification method of the invention, the functional domain or domains of a native pro-peptide is identified by localized random mutagenesis using PCR in the presence of an error-prone DNA polymerase to obtain mutations in the pro-sequence which prevent production of the biological (e.g. protease) activity. Using localized random PCR mutagenesis on the coding region of the mature protein, point mutations are introduced which suppress the inhibitory activity of the mutation in the pro-sequence. By this identification method, domains are identified within the pro-sequence which are essential to promote the folding and activation of the mature peptide into an active conformation. In accordance with the activation method, a peptide which contains one or more of the domains identified is synthesized and reacted with the native protein to produce the biochemically active protein.

Instead of using the PCR method, other identification methods may be used such as screening a panel of peptides and selecting activating ones.

In accordance with the invention, various subtilisins have been used as models in the invention. However, as described in greater detail further below, the invention is not limited to such serine proteases, but broadly includes any and all such mature polypeptides which normally require their pro-sequence for folding into an active conformation which following the teaching of the invention, can be folded from a biochemically inactive conformation into a biochemically active conformation by means of a pro-peptide which contains the essential domains discussed above.

Subtilisin is expressed in the bacterium as pre-pro-subtilisin, a precursor to the mature enzyme. The pre-peptide portion of this precursor functions in, and is essential for, the secretion of pro-subtilisin from the cytoplasm to the culture medium. The pre-peptide which consists of 29 amino acid residues and possesses the typical domain structure known for bacterial signal peptides is removed after initiating the secretion process. While the pre-peptide is not essential for the proper folding of active subtilisin, denatured subtilisin cannot be renatured in the absence of the pro-peptide. It has been found that the pro-peptide, covalently linked to the amino terminal end of the subtilisin, guides the folding of subtilisin into its biochemically active conformation in an intramolecular reaction. Also, it has been found that specific regions of the 77 amino acid pro-peptide are essential for its activity.

As described hereinafter, the teachings of the invention are broadly applicable to any biochemically active mature polypeptide which is normally, but not necessarily, expressed in precursor form with a native pro-sequence from a biochemically inactive polypeptide which does not contain its pro-sequence. Illustrative types of such polypeptides, but not limited thereto include enzymes like various proteases, polypeptide, hormones, and other peptides which need a pro-sequence or its equivalent for folding into an active conformation.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

FIG. 1 shows the amino acid sequence of pro-subtilisin E, pro-subtilisin BPN', pro-subtilisin and pro-subtilisin Carlsberg, SEQ. ID NOS.1–4.

Figure 1A:
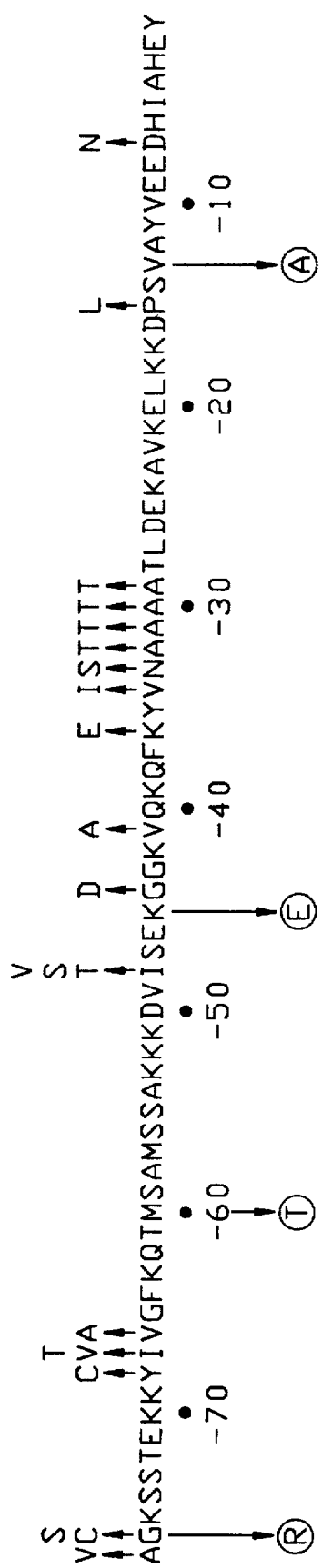
FIG. 1A shows amino acid mutations on the pro-sequence of subtilisin, SEQ. ID NO.5.

The invention is described in greater detail hereinafter.

DETAILED DESCRIPTION OF PREFERRED EMBODIMENTS OF THE INVENTION

The invention relates to biochemically or physiologically active proteins. The invention teaches a method of broad applicability to any protein which depends normally on the native pro-sequence of its precursor to be biochemically active. By this method, a biochemically inactive mature polypeptide can be rendered biochemically active by reaction with a peptide which has been especially tailor-made in that it contains one or more functional domains that are necessary to promote the folding of the mature inactive polypeptide into a biochemically active conformation. The pro-sequence need not be identical in its constitution of amino acid residues to the naturally occurring pro-sequence providing it contains one or more of the necessary functional domains that is or are present in the pro-sequence, or domains of equivalent function, but different amino acid constitution.

The strict or classic definition of a pro-sequence states that it is cleaved and is not contained in the mature protein. However, it is possible that some proteins utilize sequences which are not eventually cleaved off to fold properly. These sequences cannot be properly termed pro-sequence. However, they are functional equivalents of pro-sequences if they promote the folding of the mature polypeptide. Thus, in accordance with the invention a sequence which functions in the native state to promote proper folding is considered an activating peptide though strictly speaking, there is no pro-sequence.

The activation method of the invention comprises reacting an activating peptide target polypeptide under conditions which promote their interactions, in the case of subtilisin, the required hydrophobic interaction, e.g. high ionic strength. Preferably, the reaction is carried in the presence of an ion that is known to stabilize proteins, like calcium. The other conditions, like pH and temperatures are selected such as not to adversely affect the stability of the proteins in the reaction system. There are several suitable ways to carry out the reaction.

In accordance with the invention, the activation of a polypeptide can be carried out with several activating peptides at the same time, i.e. a polypeptide can be subjected to the action of several peptides concurrently or sequentially. Also, several polypeptides can be reacted with one or more activating peptides concurrently or sequentially.

In accordance with the invention, an activating peptide may contain more than one functional domain which contributes to the folding of a given inactive polypeptide. Thus, the activating peptide may contain one or more other functional domains which are capable of activating another given polypeptide. Thus, such hybrid activating peptide, which contain different functional domains, may conceivably activate different polypeptides. It can be envisaged that a mixture of different polypeptides can thus be activated by a given activating peptide. If desired several such activating peptides can be also used in the activation reaction of the invention.

It is not uncommon for polypeptides expressed in eukaryotic or prokaryotic cells to be inactive or partially inactive, or found in such condition, as in aggregates, that will require a separation and inactivation treatment prior to applying the activation method of the invention. Accordingly, it will not be uncommon to expose the polypeptide to be activated to a denaturant which in effect will reduce its biological activity, then in the presence of the denaturant react the activating peptide and the target polypeptide and separate the denaturant by any suitable method, as by dialysis. The activated polypeptide is separated from the activating peptide by any suitable protein purification as by gel filtration.

Requirement of the Pro- Peptide for the Production of Active Subtilisin

It will be informative now to discuss the requirements of the activating peptide using subtilisin as a model.

In the studies in conjunction with the invention the following features of the pro-sequence and the activation system have been demonstrated.

1. Removal of part or all of the pro-peptide results in the production of inactive subtilisin.

To investigate the role of the pro-peptide of subtilisin, an expression system for active subtilisin E was established in E. coli by replacing the pro-sequence of pre-pro-subtilisin with the E. coli OmpA signal peptide. Using this system, active subtilisin E was secreted into the periplasmic space. When the amino terminal 14 residues of the pro-peptide were deleted and the pro-peptide from –63 to –1 was thus fused to the OmpA signal peptide, no active subtilisin was produced. Similarly, the deletion of the amino terminal 43 residues resulted in the production of inactive mutant pro-subtilisin. In both the above cases, the shortened pro-peptides were not removed.

Further, when the entire pro-peptide was deleted and directly fusing the OmpA signal peptide to the mature subtilisin, a large amount of the polypeptide having the identical primary structure as subtilisin E was produced without any protease activity.

These studies clearly established that the pro-peptide is essential for the production of active subtilisin.

2. Processing of the pro-peptide occurs by an intramolecular, autoprocessing mechanism.

Using the *E. coli* expression system described above, pro-subtilisin could be produced in an inactive, denatured form as inclusion bodies. Pro-subtilisin thus produced was solubilized in 6M guanidine-HCl and purified to homogeneity in the presence of 5M urea.

When the purified pro-subtilisin was dialyzed against 0.2M sodium phosphate buffer (pH 6.2), it was converted to active subtilisin. Its N-terminal amino acid sequence and the mobility in SDS-polyacrylamide gel electrophoresis were identical to those of authentic subtilisin.

It is interesting to note that the processing reaction to active subtilisin was independent of the pro-subtilisin concentration. Thus, the conversion is a first-order reaction. Inhibitors such as phenylmethanesulfonyl fluoride and Streptomyces subtilisin inhibitor were unable to inhibit the processing to active subtilisin.

The mutant pro-subtilisin with the deletion of the amino-terminal 14 residues of the pro-peptide was unable to be processed into active, mature subtilisin by the in vitro processing system.

It was further found that pro-subtilisin with an active-site mutation (aspartic acid at position 32 to asparagine) was unable to be processed to active subtilisin both in vivo and in vitro.

3. The pro-peptide can guide the refolding of denatured subtilisin in an intermolecular process.

The studies established that denatured subtilisin (without the pro-peptide) cannot be renatured to active subtilisin. Similarly denatured pro-subtilisin with an active site mutation (Asp32 to Asn) cannot be autoprocessed to form mature subtilisin. However, when these two denatured proteins are mixed prior to dialysis, active subtilisin is formed. This demonstrated that the refolding of denatured subtilisin to an active enzyme can be achieved with the aid of an exogenously added pro-peptide.

The pro-peptide of pro-subtilisin E with the Asp32 to Asn active site mutation was also able to renature acid-denatured subtilisins BPN' and Carlsberg. This pro-peptide variant was effective even though there are quite a number of amino acid substitutions in both subtilisins BPN' and Carlsberg when compared with subtilisin E (See FIG. 1).

4. Synthetic pro-peptides as opposed to the native pro-peptide of a mature peptide, are able to activate inactive subtilisin to active subtilisin.

The pro-peptide of 77 residues for subtilisin E (see FIG. 1) was synthesized. This synthetic pro-peptide was able to intermolecularly complement the refolding of denatured subtilisin E to active enzyme.

Similarly, pro-peptides corresponding to −1 to −77, −1 to −68 and −1 to −63 for subtilisin BPN' were synthesized (See FIG. 1). The pro-77-mer is the most effective for the renaturation of denatured subtilisin BPN', while both pro-68- mer and pro-63- mer are nearly equally effective at approximately 30–40% of the efficiency of the pro-77-mer.

It is interesting to note that these synthetic pro-peptides for subtilisin BPN' are also able to renature subtilisin E. Thus, synthetic pro-peptides which contain the functional domain(s) are capable of renaturing other mature peptides which have enough sequence homology with the selected model for activation.

5. The synthetic pro-peptide is able to specifically bind to the active center of subtilisin.

It was shown that the synthetic pro-peptide of −1 to −77 for subtilisin E functions as a competitive inhibitor for the enzyme with an upper limit to a Ki of $5.4 \times 10^{-7}$M.

In contrast, synthetic shorter pro-peptides corresponding to −44 to −77, −1 to −64 and −1 to −43 are unable to specifically bind to the active center of subtilisin E.

The pro-77-mer (from −1 to −77), the pro-68-mer (from −1 to −68) and the pro-63-mer (from −1 to −63) for subtilisin BPN' function as competitive inhibitors with Ki's of $3.8 \times 10^{-7}$, $7.6 \times 10^{-7}$, and $7.9 \times 10^{-7}$M, respectively.

6. Refolding of denatured pro-subtilisin and its intramolecular autoprocessing to active subtilisin is sensitive to ionic strength and anions used.

The optimum conditions appear to be following. Refolding of the target polypeptide is performed for best results in phosphate buffer of higher than 0.2M at pH 6.2 or in 10 mM phosphate buffer at pH 6.2 containing higher than 0.4 $(NH_4)_2SO_4$.

The optimum condition for folding the target polypeptide is to dialyze denatured pro-subtilisin solution against 0.5M $(NH_4)_2SO_4$ and 1 mM $CaCl_2$ in 10 mM Tris-HCl buffer at pH 7.0.

$SO_4^=$ and $PO_4^=$ are much more effective than $Cl^-$ for the refolding process, while $(NH_4)_2SO_4$ can be replaced with $Na_2SO_4$, $K_2SO_4$ or $Li_2SO_4$.

FIG. 1 shows the amino acid sequences of pro-subtilisin E, pro-subtilisin BPN', subtilisin Amylosacchariticus, and pro-subtilisin Carlsberg. The entire amino acid sequence of pro-subtilisin E is shown on the top and only those amino acid residues different from pro-subtilisin E are shown for both pro-subtilisin BPN' and pro-subtilisin Carlsberg. Certain residues, not present in pro-subtilisin Carlsberg are shown by hyphens. The amino terminal end of mature subtilisin is numbered $H_2$, and therefore the pro-sequence to be numbered from −77 to −1. The autoprocessing site of the pro-peptide where the pro-sequence is cleared off is indicated by an arrow.

The structure of various other subtilisins are known. See for instance, U.S. Pat. No. 5,013,637, "Subtilisin Mutations" to Bryn et al., which is incorporated herein by reference.

Analysis of Pro-Subtilisin on Basis of Polarity

It is important to note that the amino acid sequence of the subtilisin pro-peptide is unusual and extremely biased when compared with the sequence of mature subtilisin (See FIG. 1). The identified unique features of the pro-peptide of subtilisin E may be listed as follows:

(a) The pro-peptide contains 15 Lys (no Arg), 2 His, 4 Asp and 7 Glu. This makes more than a third of the pro-peptide electrically charged (28 out of 77; 36% in contrast to 12% of the mature region).

(b) The distribution of these charged residues is extremely uneven. The amino-terminal sequence of 27 residues (−77 to −51; See FIG. 1) contains 7 Lys and only 1 Glu, while the carboxyl-terminal sequence of 16 residues (−16 to −1; See FIG. 1) contains 5 acidic residues with 2 His and no Lys residues.

(c) Ser and Thr (a total of 10 residues) are also unevenly distributed in the peptide; 7 of them are within the amino-terminal sequence of 24 residues.

(d) The pro-peptide has a relatively high content of aromatic (hydrophilic) residues: 4 Tyr plus 2 Phe.

(e) The pro-peptide contains only 1 Pro residue at position −15.

(f) The pro-peptide contains a hydrophobic sequence of 9 residues ($^{-35}$Y-V-N-A-A-A-A-T-L$^{-27}$) (SEQ. ID NO.9) at the center of the peptide, which is flanked by 2 shorter hydrophobic sequences ($^{-68}$Y-I-V-G-F$^{-64}$ (SEQ. ID NO.10) and $^{-13}$V-A-Y-V$^{-10}$) (SEQ. ID NO.11).

A Model for Protein Folding

Subtilisin is an ideal model for the studies involving the invention. Pro-subtilisin consists of 352 amino acid residues; 77 residues for the amino-terminal pro-peptide plus 275 residues for the mature subtilisin.

The tertiary structure of active subtilisin has been determined by X-ray crystallography. This structure shows that the electric charge distribution of the surface of the subtilisin is uneven. The surface region where the substrate-binding site exists contains few charged residues, i.e. Lys, Arg, Asp and Glu. Instead the region is covered by hydrophobic (non-polar) residues i.e. like Ala, Ile, Leu, Met, Phe, Pro, Trp, and Val. Although the three-dimensional structure of pro-subtilisin still remains to be determined by X-ray crystallography, the highly charged (negatively or positively) pro-peptide is most likely to cover the hydrophobic surface of subtilisin so that charged residues are distributed more evenly on the pro-subtilisin surface. Thus, the interaction between the pro-peptide and mature subtilisin is likely to result from the association of the hydrophobic regions of the pro-sequence with the hydrophobic active site of the target polypeptide.

The requirement of a high ionic strength environment for pro-subtilisin refolding in the reactivation reaction probably facilitates and stabilizes this hydrophobic interaction. The present hypothesis that the pro-peptide interacts at the active site region of subtilisin is also supported by the fact that the pro-peptide specifically binds to subtilisin as a competitive inhibitor and thus to its active center. The conformation of the subtilisin domain of pro-subtilisin may not be globally distorted from the structure of subtilisin, since pro-subtilisin is able to cleave off the pro-peptide, indicating that the active site of pro-subtilisin is functional. This also suggests that the cleavage site of the pro-peptide in the pro-subtilisin structure is at or near the active site of the subtilisin domain. Although the amino-terminal end of subtilisin is shown to be very far from the active site, it can be moved to the active site without drastically altering the subtilisin structure. The α carbon of the amino-terminal alanine residue of the mature subtilisin is approximately 26A° away from the active site triad. If the same catalytic triad is responsible for the cleavage of the pro-peptide, the alanine residue should be in the vicinity of the active site. Interestingly, the first 6 residues of the amino-terminal end of the mature subtilisin do not exhibit any specific structure, and at the 7th position there is a conserved glycine residue. This could give flexibility at the amino-terminal structure of mature subtilisin so that the amino-terminal alanine residue could come very close in folding to the active site.

As described hereinafter, it is noteworthy that the localized random mutagenesis of the identification method of the invention on the pro-peptide reveals that the first and the central hydrophobic sequences are mutational hot spots. These areas are identified as $H_1$ and $H_2$. See FIG. 2. Thus, it may be that these hydrophobic regions may play a key role in subtilisin folding by interacting with hydrophobic sequences in mature subtilisin to prevent unproductive folding within the subtilisin molecule.

DETAILED DESCRIPTIONS OF THE FIGURES

FIG. 1. Amino acid sequence of pro-subtilisin E, pro-subtilisin BPN', pro-subtilisin amylosacchariticus and pro-subtilisin Carlsberg (SEQ. ID NO.1–4). The entire amino acid sequence of pro-subtilisin E is shown on the top and only those amino acid residues different from pro-subtilisin E are shown for both pro-subtilisin BPN' and pro-subtilisin Carlsberg. Those residues not present in pro-subtilisin Carlsberg are shown by hyphens. The amino terminal end of mature subtilisin is numbered +1, and therefore, the pro-sequence is numbered from −77 to −1. The autoprocessing site of the pro-peptide is indicated by and arrow.

FIG. 1A. Pro-sequence of subtilisin showing amino acid mutations (above and below) the respective amino acids (SEQ. ID NO.5).

Figure 2:
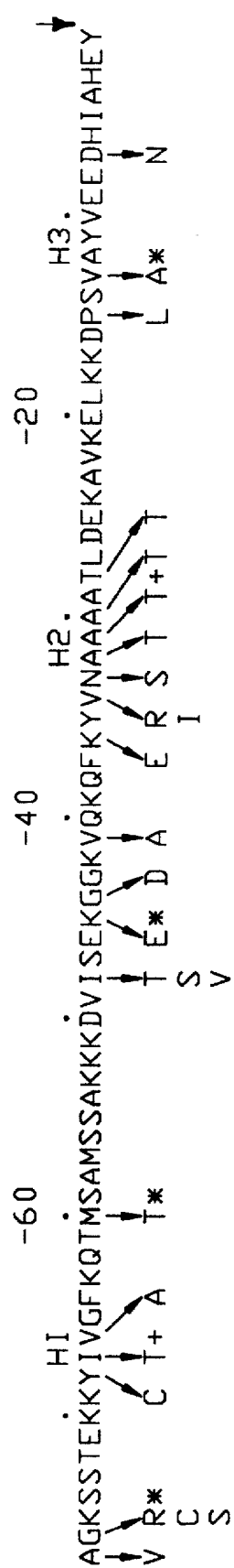
FIG. 2 shows mutations in the pro-peptide of subtilisin E, SEQ. ID NO.5.

FIG. 2. Mutations in the pro-peptide of subtilisin E. (SEQ. ID NO.5) Localized PCR random mutagenesis was carried out within the region coding the pro-peptide, using the XbaI-HindIII fragment from phI215-T. Halo-less colonies were obtained as subtilisin-negative mutants and the mutations were determined by DNA sequencing of the entire XbaI-HindIII fragment. The entire amino acid sequence of the subtilisin E pro-peptide is shown. A big arrow indicates the cleavage site of the pro-peptide. The sequence is numbered from −1 (the C-terminal end of the pro-peptide) and dotted at every tenth residue from the −1 residue. Arrows indicate the amino acid substitutions and the numbers with amino acid indicates numbers of independent mutations isolated. Mutations I(−67)T and A(−31)T were isolated together, which are marked with a plus mark. The hydrophobic sequences $H_1$, $H_2$, $H_3$ are boxed.

Figure 3:
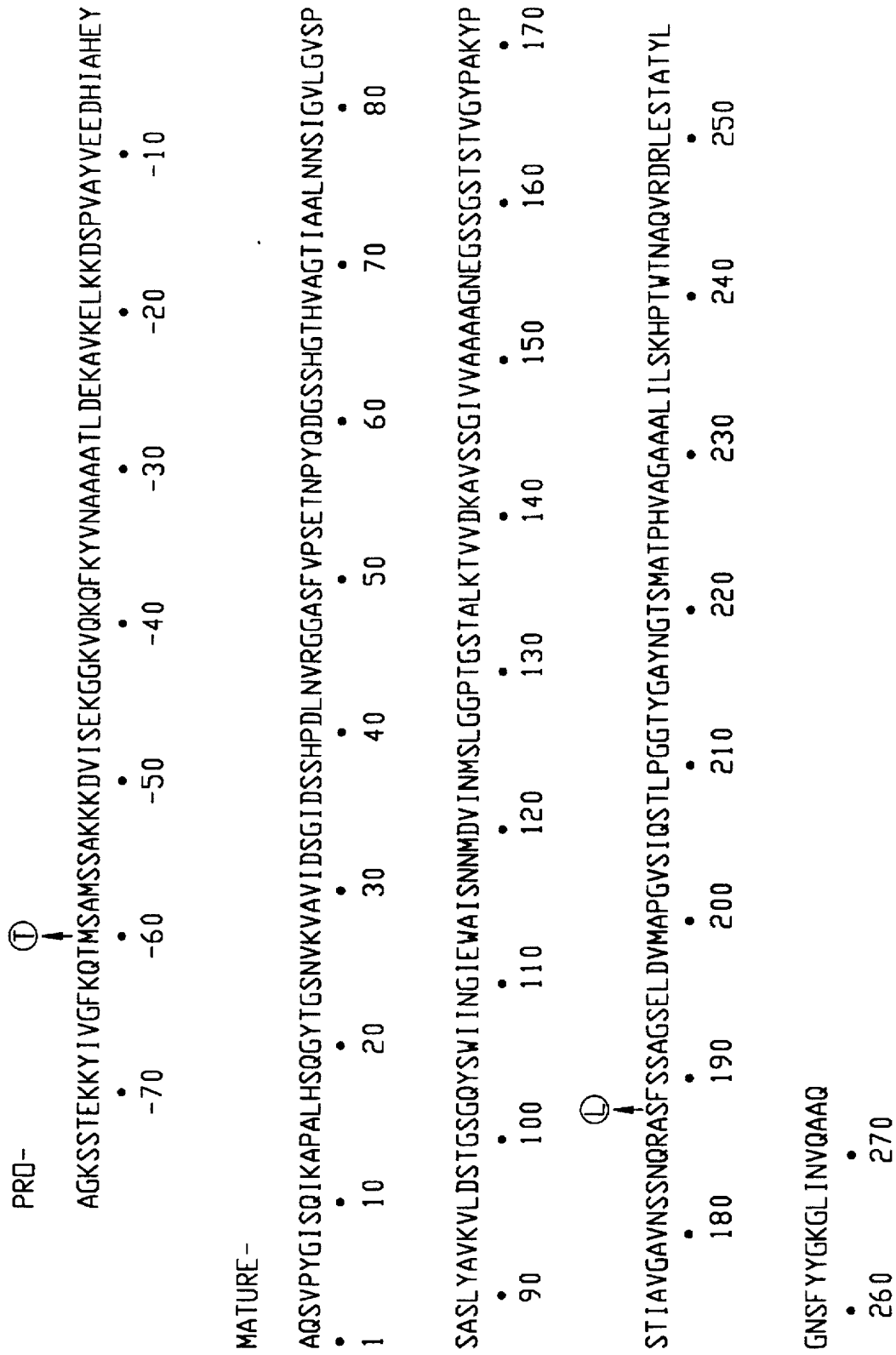
FIG. 3 shows a suppressor mutation of the Met (–60) Thr pro-sequence mutation, SEQ. ID NO.6.

FIG. 3. Shows the suppressor mutation Met (−60) Thr in the pro-sequence mutant (SEQ. ID NO.6).

Figure 4:
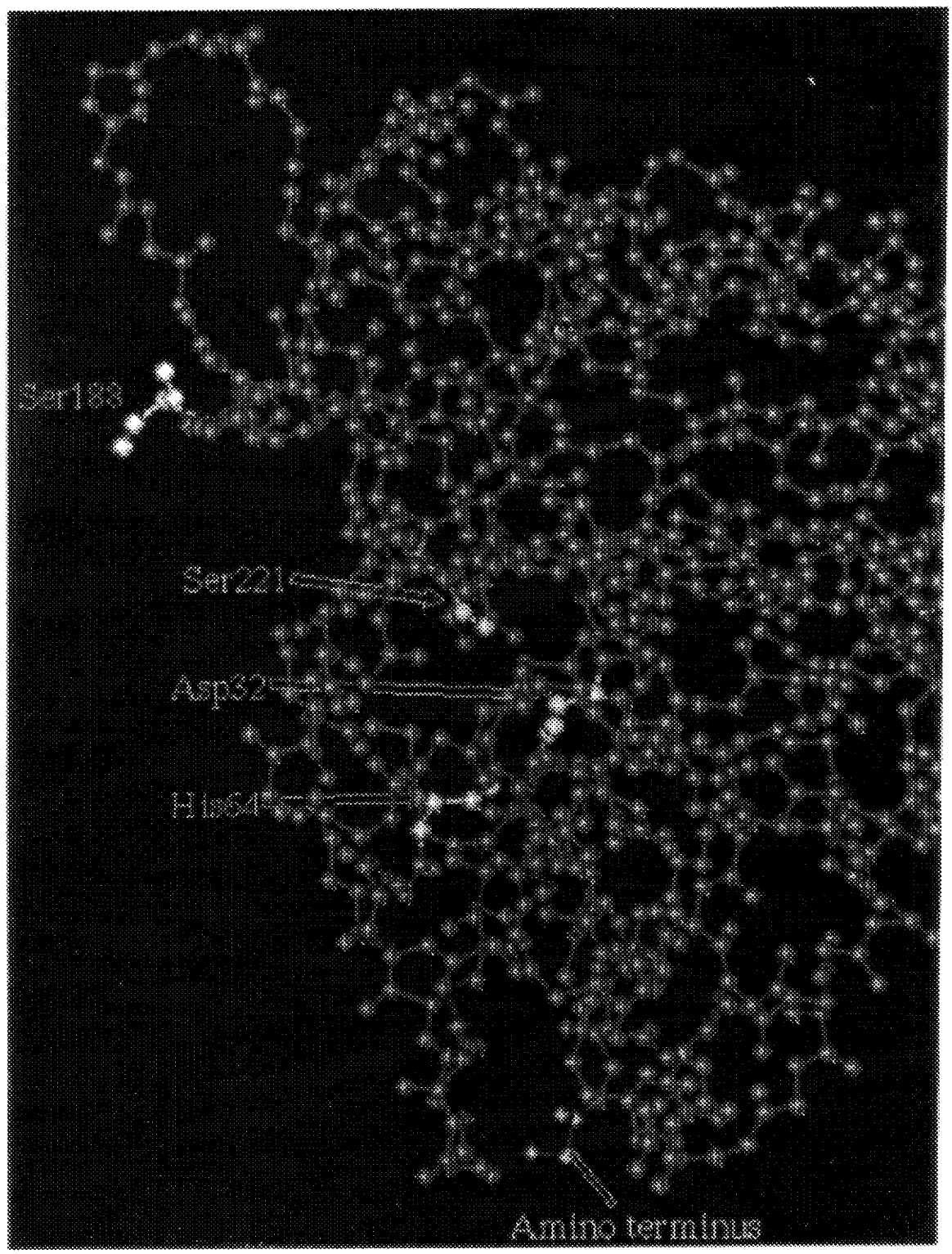
FIG. 4 shows three dimensional structure of subtilisin BPN' generated using the SYBYL software (ver. 1990).

FIG. 4. Three dimensional structure of subtilisin BPN' (ISB) generated using the SYBYL software (vet. 1990); R. A. Aldon, J. J. Briktoff, J. Kraue, J. D. Robertus, C. S. Wright, Biochem. Biophys. Res. Comm., 45, 337, (1971), Yellow indicates residues constituting the active site of subtilisin (Asp32, His 64, and Set221). Note that Ser188 (depicted white) line in a loop-like structure on the surface close to the cleft of the active site, while the amino terminus (cyan colored), where the pro-peptide is attached is away from the active site.

The Identification Method For Functional Domains For Folding

Mutational Hot Spots in the Pro-Peptide and Second-Site Suppressor Mutation with the Mature Peptide In accordance with the identification method of the invention, one or more functional domains in the pro-sequence (when the peptide has such sequence) have been identified which are essential to the folding of the target polypeptide into an active conformation. The method involves localized random PCR mutagenesis in the prosequence and in the mature polypeptide. By the first, random mutations were introduced into the pro-sequence which blocked its usual capability to assist in the folding of the polypeptide. These mutations were found in several distinct clusters. In the second PCR random mutagenesis, this one on the mature polypeptide, a mutation is introduced which suppresses (suppressor or compensatory mutation) the inhibitory effect of the mutation in the pro-sequence. The panel of resulting polypeptide each one with its fused pro-sequence are tested for biological activity. Those which have the activity restored are selected. Since mutagenesis reaction generates mutations randomly, it is highly unlikely that mutations were not introduced into other regions of the pro-sequence. These however did not influence the folding activity. It can therefore be concluded that the regions identified represent functional domains which are necessary to the folding property of the pro-sequence. By introducing and isolating many such second-site suppressor polypeptide mutations, one skilled in the art will be able to map specific domains of interaction in the pro-sequence and the mature polypeptide. From this it can be seen that the amino acid constitution of the peptide is different from that of the native pro-sequence.

Thus, in accordance with the identification method of the invention, it has been found that with respect to subtilisin, certain amino acid mutations in the pro-sequence abolish subtilisin activity. The mutations are positioned in high frequency at the hydrophobic regions of the pro-peptide. The effect of a specific pro-sequence mutation was abolished by introducing a second site suppressor mutation within the mature region of the peptide, thus, reestablishing the activity of the subtilisin.

In general, pro-peptides or activating peptides for use in the identification method of the invention are generated in vitro by random PCR amplification in the presence of an error-prone DNA polymerase introducing random mutations into the region of the gene encoding the pro-sequence of the mature peptide. Mutants that contain a variety of amino acid substitutions which are deficient in the biological (e.g. proteolytic) activity of the mature protein are isolated. Mutations within the portion of the gene encoding the mature protein are also obtained by localized random PCR mutagenesis. The resulting mutated DNA fragments are ligated to the above referred to mutated pro-sequence and colonies are selected which show the desired biological activity. These represent the mature proteins which were encoded by DNA fragments containing at least one point mutation which is compensatory or suppressive of the mutation which had folding inhibiting activity for the pro-sequence. Thus, in accordance with the invention, there are generated biological active mature peptides which have at least one amino acid mutation in the pro-sequence and at least one amino acid mutation in the mature sequence. In this manner, one or more domains in the pro-sequence which are necessary for proper folding are identified. The activating peptide which is constructed or made by DNA recombinant means will contain this single or multiple functional domain (s).

In accordance with the invention, the mutation in the pro-sequence and in the mature may be a point mutation in the nucleotide sequence resulting in a single amino acid substitution, or there may be introduced multiple point mutations, which may be contiguous or not, resulting in several amino acid substitutions which in turn, may be contiguous or not.

Utilizing localized PCR random mutagenesis, 25 different amino acid substitution mutations have been isolated which inhibit the pro-peptide mediated folding of subtilisin into its biochemically active confirmation. This procedure randomly introduces mutations within the entire length of the DNA sequence encoding the pro-peptide. Plasmids containing the mutated fragments are introduced into *E. coli* and mutations affecting pro-peptide mediated folding of subtilisin are identified as colonies lacking proteolytic activity. This is readily accomplished by spreading the cells on agar containing 2% casein, a substrate of subtilisin. Protease positive cells produce a "halo" resulting from degradation of casein in the medium. Mutations adversely influencing pro-peptide mediated folding do not produce a halo.

Analysis of the panel of pro-peptide mutations isolated according to the procedure above showed that several specific regions or domains of the subtilisin pro-sequence are essential for directing the folding of the enzyme. Mutations affecting pro-peptide activity were clustered within three hydrophobic domains contained in the pro-sequence (See FIG. 1). These regions consist of amino acids containing hydrophobic site groups, 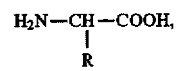 wherein R represents side groups. Typical nonpolar (hydrophobic) R groups include those of Ala, Ile, Leu, Val, Pro, Phe, Trp and Met.

Of the 20 amino acids commonly found in proteins, R varies and can consist of charged hydrophilic moieties (e.g., $R=CH_2COO^-$; neutral or moieties (e.g., $R=CH_2OH$) or hydrophobic moieties (hydrocarbon-containing, like valine).

The results of experiments described herein strongly suggest that regions of the subtilisin pro-peptide containing amino acid with hydrophobic side groups are essential for pro-peptide mediated folding of subtilisin. Three such regions have been identified, designated $H_1$, $H_2$ and $H_3$, wherein $H_1$ spans residues −68 to −64; $H_2$, residues −36 to −27 and $H_3$, residues −13 to −1. See FIG. 2. Of the 25 mutations constructed, 12 were found to occur within the hydrophobic domains $H_1$, $H_2$, $H_3$ indicating that these regions are hot spots for mutations affecting pro-peptide activity. Outside of the hydrophobic domains, 3 additional mutations occurred at hydrophobic amino acids, met (−60), ile (−48) and val (−41). Five mutations occurred at hydrophilic or neutral residues, gly (−76), lys (−45), gly (−44), lys (−36) and asp (−7). See FIG. 2.

The putative role of the hydrophobic domains of the pro-peptide is supported by previous experiments in conjunction with the invention indicating that the pro-peptide functions as a competitive inhibitor of subtilisin and thus interacts with the substrate binding cleft of the enzyme. This region of mature subtilisin also consists predominantly of hydrophobic residues.

The commence characterizing of the specific interactions which occur between subtilisin and its pro-peptide, a series of experiments were undertaken to isolate second site mutations which suppressed the folding inhibitory activity of the pre-sequence mutations described above. In these experiments, a DNA fragment encoding the subtilisin pro-peptide containing 1 of the 25 mutations previously described is attached to a DNA fragment encoding the mature subtilisin amino acid sequence. The resulting recombinant gene codes for the entire subtilisin precursor molecule (pre-pro-subtilisin). Due to the pro-sequence mutations, this construct inherently cannot produce active subtilisin. However, by introducing random mutations within the DNA fragment encoding mature subtilisin and attaching these to the mutated pro-sequence, it can be determined if mutations within the mature subtilisin coding sequence are able to suppress the inhibitory effect of the pro-sequence mutation.

Using the met (−60) to Thr mutation within the pro-sequence, a second site suppressor mutation was identified as a halo forming colony on agar containing casein, thus being protease positive. Sequence analysis of the DNA fragment from this clone encoding the mature subtilisin revealed that Ser at position 188 was replaced by a Leu residue, the result of a point mutation in the DNA sequence from TCA to TTA. See FIG. 3. This single nucleotide mutation thus suppressed the folding inhibitory activity of the original met (−60) Thr pro-sequence mutation.

This result suggests that positions −60 and 188 are located very close to one another in the native pro-subtilisin structure. X-ray crystallographic data of subtilisin has shown that ser 188 is indeed located on the surface of the subtilisin molecule near the active site cleft. Thus, the suppressor mutation isolated behaves in a manner consistent with the interaction of the activating peptide and the active site of subtilisin and residues −60 to 188 appear to be involved in this interaction.

More detailed mapping of the interactions occurring between the target polypeptide and its activating peptide can be obtained by generating additional second site suppressor mutations which compensate for the loss of folding observed with the remaining activating peptide amino acid substitution mutations. It is envisioned that such second site mutations can readily be constructed according to the methodology outlined in the present application.

The Activation Method For Reacting A Pro-Sequence With A Mature Protein

The process for refolding a biochemically inactive mature polypeptide to a biochemically active conformation comprises in general, reacting in vitro the biochemically inactive polypeptide with one or more activating peptide which contains the one or more functional domains identified as described herein under such conditions which promote their interaction. If the activating peptide and the mature protein react by hydrophobic interaction, a medium of light ionic strength will promote folding.

As described in the earlier part of this description, the origin of the target polypeptide can be quite varied. If the polypeptide has been expressed in an prokaryotic (e.g., bacterial) cell, it is generally necessary to denature the polypeptide to remove it from the cell. This will of course inactivate the polypeptide. As described herein above and abundantly in the literature, numerous procedures have been proposed to avoid such inactivation and/or reactivate such inactive polypeptides. These have not been entirely satisfactory.

In accordance with the activation method of the invention, the inactive polypeptide will be reacted with the tailor-made activating peptide containing the functional domain(s). The details of the method can readily be worked out by one skilled in the art to provide the conditions to promote the interaction of the hydrophilic or hydrophobic domain(s), that is, for hydrophobic domains, generally high ionic strength. The procedure can be carried in at least two ways. By one procedure, the inactive polypeptide can be separated from the denaturant and the polypeptide can be reacted with the synthetic tailor-made activating sequence in a medium containing appropriate salts, and if desired, stabilizing ions for the peptides. By the second procedure, the synthetic tailor-made activating sequence is mixed with the inactive polypeptide in the presence of the denaturant. The denaturant is then separated gradually by any known technique like dialysis (for molecules smaller than the peptides), allowing the activating peptide to react with the inactive polypeptides and gradually cause it to adopt a biochemically active conformation. The reaction is carried out in a medium of high ionic strength, preferably in the presence of stabilizing salts for the peptides. The duration of this procedure may be adjusted as desired, preferably slow over 12 hours or more. The progress and extent of the activation and activity of the polypeptide can be readily monitored by assaying the biological activity, e.g., enzymatic or other biological activity by known assays.

For optimum results, it appears that the second procedure is preferable. In the first procedure, as the denaturant is removed, the polypeptide may have a tendency to folding in an unproductive manner to an incompetent conformation prior to the addition of the pro-peptide. This may not be as effective as when the inactive polypeptide is fully denatured in the presence or the pro-peptide. Thus, the procedure where the reaction is carried out in the presence of a traditional denaturant, is quite suitable.

For denaturing, the protein can be treated with and, base, or high concentration of salt or a denaturing agent like high concentration of urea or guanidine. If the protein has polypeptide chains and if these are covalently cross-linked by one or more disulfide bonds between half residues of cystine, then denaturing should be done in the presence of reducing agents, such as thiothreatol or B-mercaptoethanol. These cysteine residues should be cleaved by appropriate chemical reaction. The denatured protein is then treated in accordance with the invention.

It is not necessary for the target polypeptide to be completely biochemically inactive. The activation method can be applied on a polypeptide which has biological activity to increase that activity to the desired level by the reaction of the synthetic activating sequence. However, as described above, the partially active polypeptide may be locked in a conformation which is not optimum for the activating sequence. When this is the situation, it may be preferable to denature the target polypeptide first, so that it will adopt a conformation causing functional domains whether the domain is hydrophobic or hydrophilic to be accessible for interacting with functional domain of the activating sequence.

With respect to activation of the target polypeptide, it is not necessary that it be activated completely; the activation may be carried to any degree or extent that is desired as long as it is to a higher degree or extent than the initial or starting activity. Refolding of any given single protein molecule to the conformation of the native state or to an active state can be partial and cause an increase in activity or a proportion of the given protein molecules present (e.g., 50%) may be completely refolded to the native active state, e.g., 100% activity; or both of these phenomena may take place. Regardless of which occurs, they both are within the scope of the invention. Thus, a protein can be activated from any state e.g. 50% to a higher state, e.g. 100%.

The activation method is carried out for optimum yields at low temperature, i.e., a temperate below physiological, e.g., below about 37° C., in the ranges of 2° C. to 10° C., often around 4° C. In the case of enzymes, the temperature should be below the temperature at which the enzyme, like a proteolytic enzyme, will start destroying itself enzymatically.

Other reaction conditions can be worked out by one skilled in the art without difficulty. In general, the conditions will be such as to promote retention of the developed biological activity. For instance, generally the pH is in the range of about 6 to about 8, preferably around neutral.

When the activating peptide is a synthetic peptide, it can be synthesized by any suitable chemical method including by peptide synthesizers. Pro-sequences of different lengths were synthesized by the method of Hajo et al., "Application of Protected-Peptide S-alkyl Thioester Method to the Synthesis of HU-Type DNA Binding Protein (HB$_s$)". *Peptide Chem.* 97–102 (1988) which is incorporated herein by reference.

When it is desired to make the activating peptide by recombinant DNA the methodology is known. See for instance, in the Bibliography which follows.

The following examples are illustrative of the invention and are not intended to limit its scope in any manner whatsoever. One of average skill in the art may without undue experimentation make biochemically activate other proteins by reaction with the appropriate activating peptide.

EXAMPLE 1

Activation of a Polypeptide

The method of reacting the peptide with the polypeptide to be biochemically activated is described in greater detail in our parent pending patent application which is incorporated herein by reference.

The pro-sequence of subtilisin was solubilized and purified as described in the parent application. Active subtilisin E from pH1212 was also purified and isolated as described in the parent application.

The pro-subtilisin was in solution in a denaturant like guanidine-HCl or urea to prevent autoprocesssing to active subtitisin. For best results, the work was carried out with urea.

The method for activating the polypeptide comprises contacting it with the selected activating peptide. For pro-subtilisin E the efficiency of the conversion to active subtilisin E is independent of the pro-subtilisin concentration, indicating a first order reaction. The reaction is carried out in an appropriate buffer medium. In the studies that were carried out, ammonium sulfate at concentrations in the range of about 0.3 to 0.5M was found to be very effective for the activation of the polypeptide, the concentration at about 0.5M being the most effective. At higher concentration, the ammonium sulfate appears to inhibit the proper folding of the polypeptide. When sulfate is used as the anion, there may be used as cations $Na^+$, $K^+$, and $Li^+$ or $NH_4^+$ and equivalent others. Most efficient processing was obtained with 0.5M $(NH_4)_2SO_4$ in a 10 mM Tri-HCl buffer (at pH7.0), containing 1 mM $CaCl_2$. Under these conditions, 1 mg of pro-subtilisin produced 89 U of subtilisin activity.

Preferably the activation process is carried out in the presence of an ion which has a stabilizing effect on the activating and activated polypeptides. In the case of proteolytic enzymes, the calcium ion has been found to have an important stabilizing effect. Accordingly, it is preferred for best results to carry out the activation in the presence of a calcium ion, or an equivalent ion. Calcium was used as $CaCl_2$ but other equivalent salts with a same effect can be used. Various concentrations can be used. In the case of subtilisin, 1 mM appeared to be optimum in the system used.

The theotical maximum activity for 1 mg of pro-subtilisin E is estimated to be 470 U. The conversion efficiency of pro-subtilisin to active subtilisin is thus calculated to be approximately 20%. The specific activity of the processed subtilisin is approximately half of authentic subtilisin E. This low specific activity of the processed subtilisin may be due to incomplete refolding of the subtilisin molecule and/or inactive subtilisin molecule contaminating the active subtilisin fraction. Sulfate and phosphate ions were found to be much more effective in processing of pro-subtilisin E than $Cl^-$, $K^+$, $Na^+$, $Li^+$, and $NH_4^+$.

This finding may be explained by stabilization of the protein based on the salting-out effectiveness of these ions. Preferentially, hydration may be involved in the stabilizing effect of $Na_2SO_4$ in concentrated solutions on the protein. This stabilizing effect may be due to an increase in hydrophobic interaction.

For the structure of pro-subtilisin, it is reasonable to suggest on the basis of the tertiary structure of subtilisin determined by X-ray crystallography that the relatively large, rather hydrophobic area adjacent to the substrate-binding site is covered by the highly charged pro sequence. This hydrophobic interaction between the pro-sequence and the hydrophobic area of the mature subtilisin may be facilitated by sulfate and phosphate ions, which stabilizes the structure of pro-subtilisin.

When pro-subtilisin E was dialyzed against various concentrations of sodium phosphate or ammonium sulfate, a lag phase of the processing reaction and a sudden increase in subtilisin activity at a certain high concentration were observed. These findings indicate that ionic strengths of these salts play an important role in refolding of denatured pro-subtilisin E and that high ionic strengths of these salts are very important for optimum refolding of the denatured pro-subtilisin E.

These phenomenas may be related to the onset of the hydrophobic interaction between the activating sequence and the mature subtilisin portion which is induced by high ionic strengths of phosphate and sulfate ions.

Thus, it is preferable in the method for promoting the refolding of an inactive protein like subtilisin that there be used high concentration of salts in high ionic strength which have a stabilizing action on the activating peptide. The salt promotes the hydrophobic interaction adjacent the substrate-binding site between the hydrophobic area of the pro-sequence and the polypeptide to be activated.

One skilled in the art can readily determine the optimum ionic strengths of the salts selected without undue experimentations.

While the method used in the invention has been illustrated at a neutral or alkaline pH, it can also be carried out at an acid pH in moderate or high salt concentration.

Other synthetic activating sequences were reacted with a selected polypeptide, in this case subtilisin, as described by Ohta et al. in Molecular Microbiology, 5(6), 1507–1510 (1991), which is incorporated herein by reference (and cofiled herewith). Active subtilisin was obtained.

The concentration of the activating peptide is preferably in a molar ratio of one of the activating protein to the polypeptide to be activated. At higher and lower concentration than 1 to 1, the renaturation yield was not as high; when the ratio exceeded 1, inhibition was observed. The activating peptide appears to act an inhibitor of the activated polypeptide.

Different concentrations of the different synthetic peptides were used a shown in the above-cited reference. The mixture of synthetic and polypeptide was dialyzed against 10 mM sodium phosphate, pH 7.0, that also contained 0.5M $(NH_4)_2$ SO$_4$, 2 mM CaCl$_2$ and 10 μm of 3,5-bis-trifluoromethylbenzeneboronic acid (BTFBA), a serine protease inhibitor.

EXAMPLE 2

Genetic Manipulations for Introduction of Mutations in the Pro-sequence and in the Mature Sequence of the Polypeptide.

1. Generation of pro-sequence mutations.

To isolate pro-sequence mutations, the previously established high expression system for the production of subtilisin E in *E. coli* was utilized. Mutations were introduced into the region of the subtilisin E gene encoding the pro-sequence by random PCR mutagenesis. This technique takes advantage of the relatively high rate of spontaneous raisincorporation of nucleotides by the Taq DNA polymerase. Amplification was conducted using the expression plasmid, pHI215, as the template and oligonucleotide primers of the sequences below:

Oligo 1: 5'-CCATGATTACGGATTCAC-3'(SEQ. ID NO.12)

Oligo 2: 5'-TGGGTTTGTTTCAGAAGG-3'(SEQ. ID NO.13)

A 510 bp sequence containing the subtilisin E pro-sequence was amplified by 25 cycles of PCR under standard reaction conditions in the presence of 1.5 mM MgCl$_2$ with Taq DNA polymerase using 20 mg of PstI linearized pHI215 as the template. The resulting fragment was cleaved with XbaI and HindIII, gel purified and ligated into pHI215 which has been digested with the same two restriction endonucleases. This results in replacement of the unmutated fragment with the PCR-mutated sequence. The resulting plasmid was transformed into *E. coli* JA221 and protease negative colonies were screened on agar plates containing 3% casein. Colonies lacking a halo represented the protease negative phenotype. Pro-sequence mutations of protease negative colonies were identified by sequence analysis using the dideoxy chain termination method.

Instead if Taq DNA polymerase, there may be used a reverse transcriptase if it is desired to increase the mutation rate.

2. Generation of suppressor mutations.

Mutations within the portion of the subtilisin E gene encoding the mature protein were carried out essentially as described above. Amplified fragments were digested with HindIII and BamHI to generate akbp fragment coding for the mature subtilisin E. These fragments were ligated into pHI215 [M(−60)T], containing the M/T pro-sequence mutation at position −60 which had been cleaved with the same two enzymes in order to replace the unmutated gene sequence with the PCR mutated fragment. The resulting plasmids were introduced into *E. coli* JA221 and protease activity was evaluated on agar plats containing 3% casein. Colonies exhibiting a halo represent suppressor mutations which restore protease activity. Suppressor mutations within the mature protein coding sequence were identified by sequence analysis as described above.

EXAMPLE 3

Specifically, the mutants were generated as follows. Localized random PCR mutagenesis was using Taq DNA polymerase within the pro-peptide coding region. For this purpose, the HindIII site within the mature subtilisin coding region was eliminated by changing the codon for Ala(46), GCA to GCT. Subsequently, the sequence CAATCTGTT for Gln-Ser-Val was altered by oligonucleotide mutagenesis to CAAAGCTTT to create a new HindIII site. This alteration resulted in an amino acid substitution at position +4 from Val to Phe which caused no effect on the subtilisin activity as assessed by the size of halo produced around a colony grown on a casein-containing plate. The plasmid containing the new HindIII site was designated pHI215T.

See FIG. 1 of Lerner et al. cited supra. (and incorporated herein by reference).

Using pHI215T, PCR random mutagenesis was carried out between the XbaI site (immediately upstream of the initiation codon) and the new HindIII site. Out of 1,300 transformants, 54 halo-less colonies were obtained (4.2%). Of 54, 31 were in-frame base-substitution mutations within the pro-peptide of which 33 were independent as shown in FIG. 2. Some mutations occurred more than once as indicated by the numbers, and both I(−67)T mutations were accompanied with the A(−31)T mutation. Four mutations previously isolated are also shown in 1A of which V(−13)A was isolated again in the present study. All mutations resulted from a single base substitution except that R at position −34 (CGT) was derived from GTT for V by 2 base substitutions.

Altogether, mutations occurred at 20 different positions and at 4 positions more than 1 mutation was isolated; G at −76 to R, C or S; I at −67 to V to T; at −48 to T, S or V; and V at −34 tp R or I. The subtilisin E pro-peptide has a primary sequence distinctly different from the subtilisin sequence. The notable features of the pro-peptide were described above.

Out of 26 mutations, 12 were found in the hydrophobic sequences, H$_1$, H$_2$, and H$_3$ (46%), indicating that these sequences are hot spots for mutations. In particular, substitutions of every Ala residue in the H$_2$ region with Thr resulted in a defective pro-peptide [in the case of A(−31)T, accompanied with I(−67)T]. This suggests that these hydrophobic sequences play a key role in guiding the subtilisin folding.

Outside the H regions, there are 3 mutations at hydrophobic residues: M(−60)T, I(−48)T, S or V, and V(−41)A. In addition, there are 5 charge mutations involving charged (hydrophobic or neutral) residues: G(−76)R, K(−45)E, G(−44)D, K(−36)E, and D(−7)N. It is also interesting to note that the mutation [P(−15)L] at the only Pro residue in the pro-peptide occurred most frequently. Mutations at positions −77 and −76 may have some effects on the cleavage of the signal peptide, thus, secondarily resulting in defective pro-peptides.

Second-site mutations were isolated which suppress the folding inhibitory activity of the pro-sequence mutations as follows.

Using the M(−60)T mutation, second-site suppressor mutations within the mature subtilisin region were isolated. This was achieved by PCR random mutagenesis in the mature subtilisin coding region. The 0.93-kb HindIII-BamHI fragment of pHI215T [M(−60)T] which encompasses the coding region of the mature subtilisin was replaced with the PCR-amplified HindIII-BamHI fragment. Out of 1,500 transformants, 1 halo-forming colony in a casein plate was isolated. DNA sequencing of this plasmid DNA from this colony revealed that Ser at position 188 was replaced by a Leu residue (TCA to TTA). See FIG. 3. The suppressor S(188)L mutation appears to be compensatory to M(−60)T. It is possible that these 2 residues at −60 and 188 may indeed be located very close to one another in the pro-subtilisin structure. It is also interesting to point out that Ser 188 is located on the surface of the subtilisin molecule near the active center cleft. Since the synthetic pro-peptide functions as a competitive inhibitor with a Ki of $5.4 \times 10^{-7}$M, the pro-peptide is likely to bind to the side where the active center is exposed.

Amino acid substitution mutations within pro-peptide can be performed by the method described in "Isolation of Subtilisin Pro-Sequence Mutations that Affect Formation of Active Protease by Localized Random Polymerase Chain Reaction Mutagenesis", Lerner et al., *The Journal of Biological Chemistry*, 265, (33), 20085–2086 (1990). The publication is incorporated herein by reference (and cofiled herewith).

Following this procedure random amino acid mutations can be introduced into a DNA sequence coding for selected pro-sequences of the associated polypeptide synthetic amino acid sequence. Likewise, suppressor mutations are introduced into the DNA sequence coding for the mature target polypeptide.

Other proteins which require their pro-sequence for the production of the biochemically active counterpart mature protein can be reacted in a similar manner. For instance, α-lytic protease and carboxy peptidase Y can be reacted with the appropriate activating peptide to render the peptide biochemically active.

By this procedure random amino acid mutations can be introduced into an amino acid sequence 166 amino acid long (166 pro-region of α-lytic protease) and suppressor mutations be introduced into the mature portion of α-lytic protease. Following the procedure described above, colonies are selected which show protease activity indicating which colonies can generate peptides which contain the functional domains which can promote the folding of the mature protein into an active configuration.

Likewise, hormones which have a pro-sequence or a sequence functionally equivalent thereto necessary for adopting a biochemically active conformation may be processed in accordance with the invention.

For enzymes which can benefit of the teaching of the invention, reference is made to *The Enzymes*, edited by Paul D. Boyer, Volume III, Academic Press, 1971, which discloses various classes of enzymes such as: Carboxypeptidase A, Carboxypeptidase B, Leucine Aminopeptidase and Other N-Terminal Exopeptidases, Pepsin, Chymotrypsinogen, Trypsin, Thrombin and Prothrombin, Pancreatic Elastase, Cathepsins and Kinin-Forming and Destroying Enzymes, Streptococcal Proteinase, Collageneses, and Clostripain.

When in accordance with the invention, an activating peptide is effective to activate a given polypeptide, it is possible that it will be effective also to activate another polypeptide which has a certain degree of amino acid homology with the given polypeptide. Purely as illustrative example, the various subtilisins are described in U.S. Pat. No. 5,013,657 (which is incorporated herein by reference) which have degree of amino acid homology varying from 50 to over 80 percent. Methods in Enzymology, 119, Interferons, Pestka discusses the various interferons and their consensus sequences. The possibility should not be excluded that in certain circumstances an activating peptide would activate several peptides that are similar enough by virtue of their consensus sequences.

As described, the invention is broadly applicable to the biochemical activation of polypeptides whether known to date or yet to be discovered. Also described, it is contemplated that the polypeptide need not have a pro-sequence as such as traditionally defined, but may have an amino acid sequence (or residue) which affects the folding of the polypeptide. The invention is also applicable to peptides which have pro-sequences like for illustration purposes and not by way of limitation, to enzymes that belong to the seine protease family, to subtilisin-like proteases, for instance Kex2 (a $Ca_{2+}$-dependent serine protease belonging to the subtilisin family), converteases, furin, PC1 and PC2, referred to in "Pro-Protein and Pro-Hormone Converteases of the Subtilisin Family, Recent developments and Future Perspectives, Seidah et al., *Trends in Endocrinology and Metabolism* (1991). Brenner et al., "Structural and Enzymatic Characterization of a Purified Hormone-Processing Enzyme: Secreted, Soluble Kex2 Protease", *Proc. Natl. Acad. Sci.*, 89, 922–926 (1992).

Other illustrative peptides to which the invention can be applied if they need a sequence to promote folding, polypeptide hormones which are usually synthesized in the form of an inactive precursor molecule (pro-hormones); e.g. endocrine and neuroendocrine processing enzymes, e.g. βLPH, αLPH and βMSH, interferons, insulin, various other hormones of medical importance, such as listed in Applications in Biotechnology, Ouellette et al.; Technomics Publishing Co., Inc. (1985); plasma proteins like β-lipoprotein, gamma globulin, and others.

A suitable protocol for one skilled in the art to follow to apply the teachings of the invention is as follows.

The first step is to amplify the DNA that encodes the pro-sequence (or its equivalent sequence). Next is to insert the amplified segment into a self-replicating vector (e.g. plasmid) which already contains the mature DNA portion, giving the complex DNA segment coding for the polypeptide except that the pro-sequence has a mutation(s). Then the cells are made to express the polypeptide and negative colonies are selected (by an appropriate assay for the biochemical property sought). Thereafter, the site mutation(s) is determined by DNA sequence analysis. The protocol is then applied to obtain a mutated mature portion of the DNA encoding in the mature portion of the polypeptide. The mutated portion that encodes the mature portion is amplified, then inserted into a self-replicating vehicle (an appropriate plasmid) which contains the mutated prosequence, thus containing the mutated pro-sequence and the mutated mature sequence. Cells are made to express the polypeptide and colonies are screened by a selected assay for positive activity sought for Positive colonies are selected. Thus, the suppressive mutation has been identified and by it the site(s) in the pro-sequence, thus identifying the functional domain. Thereafter, the functional domain(s) are built into a peptide (the peptide construct containing the functional domain(s)). This peptide—the activating peptide—is constructed by synthetic or DNA recombinant methods.

The activating peptide coding for the selecting prosequence and the polypeptide is made to express the polypeptide and assayed for activity.

The resulting activating peptide is then reacted, preferably in the presence of a denaturant for the polypeptide under conditions which promote the interaction of the two molecules. If the functional domains are hydrophobic, the reaction condition will promote such reaction; if hydrophobic, then the conditions will be correspondingly selected. The desired peptide is separated from the activating peptide and isolated and kept under conditions maintaining the regained or increased biochemical activity. The polypeptide may be a novel polypeptide and not identical in structure or activity to the native polypeptide. The activity will have been increased or even a new biochemical activity may have come about.

In this manner, human renin could be activated to its biochemically active form.

Following the procedure taught above, carboxypeptidase after denaturation, could be reactivated by an appropriate activating peptide. The procedure could be applied to reactivate porcine pepsinogen. The method could be applied to other peptides discussed in the literature which have a pro- or a functionally equivalent sequence.

It is to be understood that while the description herein has been made of preferred embodiments, the present invention is not to be limited thereto but is intended to cover all embodiments (including methods and/or products) which come within what is called the doctrine of equivalents.

Publications which are listed below in the Bibliography are incorporated herein by reference.

BIBLIOGRAPHY

1. Ausubel et al., "Current Protocols In Molecular Biology", *Greene Publishing Associates and Wiley-Interscience*, Vols. 1 2 and 3 (1989).
2. Barr P. J., Mammalian Subtilisin: "The Long Sought Dibasic Processing Endoproteases, *Cell*, 66, 1–3 (1991).
3. Boyer P. D. The Enzymes, *Academic Press*, Vol. III (1971).
4. Boyer, H. W. & Carton B. C., "Production of Two Proteolytic Enzymes by a Transformable Strain of *Bacillus subtilis*", *Arch. Biochem. Biophys*, 128, 442–445 (1968).
5. Brenner et al., "Structural and Enzymatic Characterization of a Purified Hormone-Processing Enzyme: Secreted, Soluble Kex2 Protease", *Proc. Natl. Acad. Sci.*, 89 922–926 (1992).
6. Cash P. W. et al. "Synthesis of the Pro-Peptide of Subtilisin BPN'", *Peptide Research*, 2, 292–296 (1989).
7. Creighton T. E., "Up the Kinetic Pathway", *Nature* 356, 192–193 (1992).
8. Drenth J. et al., "Subtilisin Novo: The Three-Dimensional Structure Ad Its Comparison With Subtilisin BPN'", *Eur J. Biochem*, 26, 177–181 (1972).
9. Ellis J., "The Molecular Chaperone Concept", *Seminar in Cell Biol*, 1, 1–9 (1990).
10. Guthrie and Fink, Eds., Academic Press, "Guide to Yeast Genetics and Molecular Biology", *Methods in Enzymology* (1991).
11. Gierasch L. M., King J., "Protein Folding, Deciphering the Second Half of the Genetic Code", *American Association for the Advancement of Science* (1990).
12. Hajo et al., "Application of Protected-Peptide S-alkyl Thioester Method to the Synthesis of HU-Type DNA Binding Protein (HB$^S$)", *Peptide Chem.*, 97–102 (1988).
13. Ikemura H., Inouye M., "In Vitro Processing of Pro-Subtilisin Produced in *Escherichia coli*", *J Biol Chem*, 263, 12959–12963 (1988).
14. Ikemura H. et al., "Requirement of Pro-Sequence for the Production of Active Subtilisin E in *Escherichia coli*", *J. Biol Chem*, 262, 7859–7864 (1987).
15. Inouye M., "Intramolecular Chaperone: The Role of the Pro-Peptide in Protein Folding", *Enzyme*, in press.
16. Jacobs M. et al., "Cloning, Sequencing and Expression of Subtilisin Carlsberg from *Bacillus licheniformis*", *Nucl Acids Res*, 13, 8913–8922 (1985).
17. Kim P. S., Baldwin R. L., "Intermediates in the Folding Reactions of Small Proteins", *Ann Rev Biochem* (1990).
18. Lerner et al., "Isolation of Subtilisin Pro-Sequence Mutations that Affect Formation of Active Protease by Localized Random Polymerase Chain Reaction Mutagenesis", *The Journal of Biological Chemistry*, 265, (33), 20085–2086 (1990).
19. Lin et al., "Synthesis, Purification, and Active Site Mutagenesis of Recombinant Porcine Pepsinogen", *The Journal of Biological Chemistry*, 264, 97–102 (1988).
20. Norman et al. "Stable Expression, Secretion, and Characterization of Active Human Renin in Mammalian Cells", *Mol. Pharmacol*, 41, 53–59 (1992).
21. Ohta Y., Inouye M., "Pro-Subtilisin E: Purification and Characterization of Its Autoprocessing to Active Subtilisin E *In Vitro*", *Mole Micro*, 4, 295–304 (1990).
22. Ohta Y. et al., "Pro-peptide As An Intermolecular Chaperone Renaturation of Denatured Subtilisin E With A Synthetic Pro-Peptide", *Molecular Microbiology*, 1507–1510 5 (6) (1991).
23. Ouellette et al.; Technomics Publishing Co., Inc. (1985)
24. Rothman J. E., "Polypeptide Chain Binding Proteins: Catalysts of Protein Folding and Related Processes in Cells", *Cell*, 59, 591–601 (1989).
25. Roy et al., "Investigation of a Possible Role of the Amino-Terminal Pro-Region of Proopiomelanocortin in its Processing and Targeting to Secretory Granules", *Molecular and Cellular Endocrinology*, 82, 237–250 (1991).
26. Sambrook et al., "Molecular Cloning: A Laboratory Manual", *Cold Spring Harbor Laboratory Press* Second Edition (1989).
27. Sanger et al., *Proc. Natl. Acad. Sci. U.S.A.*, 74, 5463–5467 (1977).
28. Seidah N. G., Chretien M., "Pro-Protein and Pro-Hormone Convertases of the Subtilisin Family: Recent Developments and Future Perspectives", *Trends Endocrinol Metabolism*, in press (1991).
29. Silen J. L. et al. "Analysis of Pre-pro-α-lytic Protease Expression in *E. coli* Reveals that the Pro Region is Required for Activity", *J. Bact*, 171, 1320–1325 (1989).
30. Silen J. L., Agard D. A., "The α-lytic Protease Pro-Region Does Not Have A Physical Linkage to Activate the Domain *In Vitro*", *Nature*, 341, 462–464 (1989).
31. Silen J. L., and Agard D. A., "The α-lytic Protease Pro-Region Does Not Require A Physical Linkage to Activate the Protease Domain *In Vivo*", *Nature* 341, 1320–1325 (1989).
32. Stahl M. L., Ferrari E., "Replacement of the *Bacillus subtilis* Subtilisin Structural Gene With An *In Vitro*-Derived Deletion Mutation", *J. Bacteriol.* 158, 411–418 (1984).
33. Takagi, H. et al., "The Role of Pro-239 in the Catalysis of Heat Stability of Subtilisin E., *J. Biochem* (Tokyo), 105, 953–956 (1989).
34. Vasantha N. et al., "Genes for Alkaline Protease and Neutral Protease from *Bacillus amyloliquefaciens* Contain a Large Open Reading Frame Between the Regions Coding for Signal Sequence and Mature Protein", *J. Bacteriol*, 158, 811–819 (1984).
35. Wakefield et al. "Addition of a C-Terminal Extension Sequence to Transforming Growth Factor-β1 Interferes with Biosynthetic Processing and Abolishes Biological Activity", *Growth Factors*, 5, 243–253 (1991).
36. Wells J. A. et al., "Cloning, Sequencing, and Secretion of *Bacillus amyloliqulfacien* subtilisin in *Bacillus subtilisin*", *Nucl Acids Res*, 11, 7911–7925 (1983).
37. Winther J. R., and Sorensen P., "Pro-Peptide of Carboxypeptidase Y Provide a Chaperone Like Function As Well As Inhibition of the Enzymatic Activity", *Proc. Natl. Acad. Sci. U.S.A.*, 88, 9330–9337 (1991).

38. Wong S. L., and Doi R. H., "Determination of the Signal Peptidase Cleavage Site in the Pre-Pro-Subtilisin of *Bacillus subtilus*", *J. Biol Chem*, 261, 10176–10181 (1986).

39. Wright C. S. et al., "Structure of Subtilisin BPN' at 2.5 A Resolution", *Nature*, 221, 235–242 (1972).

40. Zhu X. et al., "Pro-Sequence of Subtilisin Can Guide the Refolding of Denatured Subtilisin in an Intermolecular Process", *Nature*, 339, 483–484 (1989).

I claim:

1. An in vitro method to restore or increase the natural biological activity of a target polypeptide, which is normally expressed containing a prosequence, which target polypeptide is biologically inactive or has decreased natural biological activity due to improper folding of the polypeptide, which method comprises reacting intermolecularly in a buffered ionic aqueous medium, thereby favoring hydrophobic interaction, an exogenous activating peptide with the target polypeptide, wherein the activating peptide has the amino acid sequence of the prosequence of the target polypeptide or of a polypeptide which has the same function as the target polypeptide and which is similar in amino acid sequence to the target polypeptide, whereby the activating peptide promotes refolding the target polypeptide into its biologically active conformation.

2. The method of claim 1 wherein the reaction is in a buffered ionic aqueous medium, thereby favoring hydrophobic interaction, and wherein the activating peptide contains a hydrophobic, non-polar region which comprises at least one amino acid containing a hydrophobic side group $H_2N$—$CH(R)$—$COOH$, wherein R is a hydrophobic group, and the target polypeptide comprises a hydrophobic site.

3. The method of claim 2 wherein the medium comprises calcium ion and an anion selected from the group consisting of sulfate and phosphate.

4. The method of claim 2 wherein the medium has a neutral or alkaline pH.

5. The method of claim 2 wherein the medium comprises a denaturant.

6. The method of claim 2 wherein the amino acid containing a hydrophobic side group is alanine, isoleucine, leucine, valine, proline, tryptophan, phenylalanine, or methionine.

7. The method of claim 1 wherein the ratio of the polypeptide to the activating peptide is about 1:1.

8. The method of claim 1 wherein the reaction is carried out at a temperature below 37° C.

9. The method of claim 1 wherein the target polypeptide is a member of the serine protease family.

10. The method of claim 9 wherein the target polypeptide has the amino acid sequence of a member of the subtilisin family.

11. The method of claim 1 wherein the activating peptide has the activity of the natural prosequence of the target polypeptide to promote the folding of the polypeptide to its biologically active conformation.

12. The method of claim 11 wherein the activating peptide has the region of amino acids which the prosequence of the target polypeptide possesses which promotes the folding of the target polypeptide into its biologically active conformation.

13. The method of claim 12 wherein the activating peptide has the amino acid sequence of the prosequence of the target polypeptide.

14. The method of claim 12 wherein the activating peptide has a structure different from that of the prosequence which normally activates the target polypeptide by promoting its folding to its biologically active conformation.

15. An in vitro method to restore or increase the natural biological activity of a target polypeptide, which is normally expressed containing a prosequence, which target polypeptide is biologically inactive or has decreased natural biological activity due to improper folding of the polypeptide, which method comprises reacting intermolecularly in a buffered ionic aqueous medium, thereby favoring hydrophobic interaction, an exogenous activating peptide with the target polypeptide, wherein the activating peptide comprises an amino acid sequence that is substantially identical to a major portion of the amino acid sequence of the natural prosequence of the target polypeptide or of the prosequence of a polypeptide that is similar in amino acid sequence to the target polypeptide and has the same function as the target polypeptide, whereby the activating peptide promotes refolding the target polypeptide into its biologically active conformation.

16. The method of claim 15 wherein the reaction is in a buffered ionic aqueous medium, thereby favoring hydrophobic interaction, and wherein the activating peptide contains a hydrophobic, non-polar region which comprises at least one amino acid containing a hydrophobic side group $H_2N$—$CH(R)$—$COOH$, wherein R is a hydrophobic group, and the target polypeptide comprises a hydrophobic site.

17. The method of claim 16 wherein the activating peptide comprises the hydrophobic amino acid sequence Val-Ala-Tyr-Val (VAYV), as shown in Seq. ID No. 11.

18. The method of claim 16 wherein the activating peptide further comprises the hydrophobic amino acid sequence Tyr-Ile-Val-Gly-Phe (YIVGF), as shown in Seq. ID No. 10.

19. The method of claim 16 wherein the activating peptide further comprises the hydrophobic amino acid sequence Tyr-Val-Asn-Ala-Ala-Ala-Ala-Thr-Leu (YVNAAAATL), as shown in Seq. ID No. 9.

20. The method of claim 15 wherein the target polypeptide is selected from the group consisting of carboxypeptidase A, carboxypeptidase B, leucine aminopeptidase, N-terminal exopeptidases, pepsin, chymotrypsinogen, thrombin, prothrombin, pancreatic elastase, cathepsins, kinin-forming and kinin destroying enzymes, streptococcal proteinase, collagenases, clostripain and renin.

21. The method of claim 15 wherein the region of the pro-sequence of the target polypeptide which promotes refolding of the target polypeptide to its biologically active conformation is identified by introducing a random mutation in the pro-sequence which mutation inhibits the folding of the polypeptide, thereby establishing that the pro-sequence possesses the region which promotes the refolding of the target polypeptide into the biological active conformation.

22. A method of making a biologically active polypeptide which method comprises treating a biologically inactive or partially inactive polypeptide with an exogenous peptide sequence by incubating said inactive polypeptide with the exogenous peptide sequence, which exogenous peptide sequence intermolecularly complements folding of said polypeptide into the biologically active polypeptide, in which the exogenous peptide sequence comprises an amino acid sequence that is substantially identical to a major portion of the amino acid sequence of the prosequence of the inactive polypeptide or of the prosequence of a polypeptide that is similar in amino acid sequence to the target polypeptide and has the same function as the target polypeptide.

23. The method of claim 22 in which the exogenous peptide sequence comprises the pro-sequence of the inactive or partially inactive polypeptide.

* * * * *